United States Patent [19]

Tinney et al.

[11] 4,287,340

[45] Sep. 1, 1981

[54] DIHYDRO-OXO-PYRIDO[1,2-A]THIENOPYRIMIDINE COMPOUNDS

[75] Inventors: Francis J. Tinney; David T. Connor; Wiaczeslaw A. Cetenko; Joseph J. Kerbleski; Roderick J. Sorenson, all of Ann Arbor, Mich.

[73] Assignee: Warner-Lambert Company, Morris Plains, N.J.

[21] Appl. No.: 132,603

[22] Filed: Mar. 21, 1980

Related U.S. Application Data

[62] Division of Ser. No. 70,227, Aug. 27, 1979, Pat. No. 4,230,707.

[51] Int. Cl.$^3$ ............................................. C07D 495/14
[52] U.S. Cl. .................................................... 544/250
[58] Field of Search ........................... 544/250; 424/251

[56] References Cited

U.S. PATENT DOCUMENTS

| 3,318,881 | 5/1967 | Ohnacker et al. ............... 424/251 X |
| 3,318,883 | 5/1967 | Ohnacker et al. ............... 424/251 X |

FOREIGN PATENT DOCUMENTS

8408  3/1980  European Pat. Off. ................. 424/251

OTHER PUBLICATIONS

Shvedov, et al., Chemical Abstracts, vol. 83, 164119k (1975).

Blaskiewicz, et al., chemical Abstracts, vol. 83, 206324f (1975).

*Primary Examiner*—Donald G. Daus
*Assistant Examiner*—Diana G. Rivers
*Attorney, Agent, or Firm*—Stephen Raines

[57] ABSTRACT

Oxo-pyrido[1,2-a]thienopyrimidine compounds, salts thereof, methods of production, intermediates in their production, pharmaceutical compositions containing said compounds and methods for treating allergies using said compositions are disclosed.

4 Claims, No Drawings

DIHYDRO-OXO-PYRIDO[1,2-A]THIENOPYRIMIDINE COMPOUNDS

This is a division, of application Ser. No. 070,227 filed Aug. 27, 1979, now U.S. Pat. No. 4,230,707.

SUMMARY AND DETAILED DESCRIPTION

The present invention relates to new oxo-pyrido[1,2-a]-thienopyrimidine compounds that are useful as anti-allergy agents, intermediates in their production, methods for their production, pharmaceutical compositions containing said anti-allergy agents and methods for treating allergic conditions with said compositions. More particularly, the invention relates to new oxo-pyridio[1,2-a]thienopyrimidine compounds of the formulae.

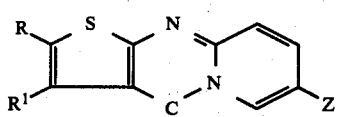

I.

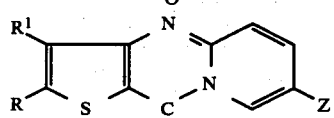

II.

and

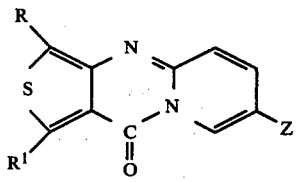

III.

and salts thereof, where R and $R^1$ are hydrogen, lower alkyl, chloro, bromo, phenyl, or X-substituted phenyl where X is lower alkyl, chloro, fluoro, or lower alkyl-O- and Z is

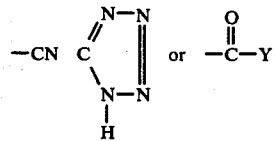

wherein Y is —OH, —NH$_2$, —O— lower alkyl or

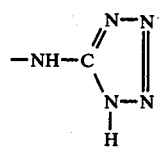

The term "lower alkyl" is intended to mean a hydrocarbon moiety which may be straight, branched or cyclic in configuration having from one to six carbon atoms.

The term "salts" is intended to mean salts formed by the addition of a base with those compounds of the invention capable of forming a salt, such as those compounds containing a carboxy or tetrazole group. Typical salts would be the sodium, potassium, calcium, ammonium, organic amino, magnesium, etc. salt. The preferred salts are relatively non-toxic, thus pharmaceutically acceptable salts, preferably the sodium salt. Compounds of this invention may form acid addition salt with strong acids, such as hydrochloric acid.

The preferred compounds of the invention are those wherein R is hydrogen, lower alkyl or phenyl and $R^1$ is hydrogen or lower alkyl.

Certain of the compounds of this invention are capable of existing in the form of hydrates or solvates. For the purposes of this invention, these other forms of the compounds are considered equivalent to the non-hydrated or non-solvated compounds and are intended to be encompassed within the scope of the invention.

The compounds of the invention may be prepared by various routes. The compounds of formulae I to III and salts thereof, except in the case of formula III where R or $R^1$ is chloro, bromo or hydrogen, are preferably prepared by reacting an appropriately substituted (amino) (lower alkoxy carbonyl) thiophene compound with a 6-halo-3-Z-pyridine compound wherein Z is as previously defined.

Compounds of the formula I and salts thereof may be prepared by reacting a compound of the formula:

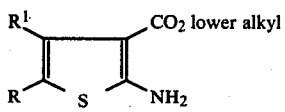

IV.

with a compound of the formula

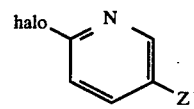

V.

wherein halo is chloro, bromo, iodo or fluoro, preferably chloro and R,$R^1$ and Z are as previously defined. The reaction temperature is from about 130° C. to about 190° C. and reaction time is one-half hour to twenty-four hours, preferably 170° to 180° C. for from two to eight hours. The reaction may be run neat or conducted in a high boiling acidic solvent, such as phenol. The ratios of reactants are not critical and approximately equimolar concentrations are employed. This procedure is preferred wherein Z is —CO$_2$H,—CONH$_2$ and —CO$_2$-lower alkyl.

The starting materials employed in the above process of the formula IV are either known or readily prepared by reacting a compound of the formula.

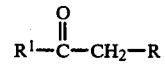

VI.

with ethyl or methyl cyanoacetate in the presence of sulfur and a secondary or tertiary amine.

The starting materials employed in the above process of the formula V are commerically available, such as those wherein Z is —COOH or CO$_2$-lower alkyl or readily prepared from these two available materials by standard procedures, such as reaction with aminotetrazole, ammonia, conversion to a nitrile followed by treatment with an azide, etc.

In addition, the compounds of the invention of formula I can be prepared using the above procedure wherein Z is cyano and converting the product of the formula

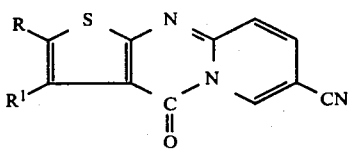

into a compound of the invention by partial hydrolysis employing aqueous strong base and heat followed by acidification to give an amido compound or complete hydrolysis employing aqueous strong acid and heat to give a carboxy compound.

Other methods wherein compounds of the invention can be converted to other compounds of the invention also involve interconversions of the Z group. More specifically, the carboxyl containing compounds of the formula I may be converted to the corresponding esters of the formula I via acid (hydrochloric, benzenesulfonic, etc.) catalysted reactions in inert solvents at temperatures of from about 10° C. to the reflux temperature of the solvent for from fifteen minutes to twenty-four hours. The carboxylic acid esters may be converted to the free acids of the invention by use of strong bases (sodium hydroxide, potassium hydroxide, etc.) in inert solvents followed by acidification.

The nitrile of the formula I can be prepared by dehydrating the corresponding amide.

A carboxylic acid of formula I can be converted to a carboxamidotetrazole of formula I by initially converting the carboxylic acid to a reaction intermediate by coupling it with at least one equivalent of 1,1'-carbonyldiimidazole or other coupling agent. The reaction takes place in a polar solvent, such as dimethylformamide for from one to sixteen hours at a temperature of from about 40° C. to about 110° C., preferably one hour at 70° C.

The 5-aminotetrazole to be coupled to the above imidazolide is preferably silylated using a silylating agent, such as trimethylchlorosilane and an organic or inorganic base, such as trialkylamine in a polar solvent, such as dimethylformamide for a period of from thirty minutes to two and one-half hours at from 0° C. to 25° C., preferably one hour at 0° C. to 5° C.

The two components are combined in a polar solvent, such as dimethylformamide, for periods of from four to seventy-two hours at about room temperature to 110° C., preferably fourteen hours at room temperature.

Lastly, the nitrile of formula VII may be converted to tetrazole compounds of the formula I wherein the tetrazole is linked directly to the pyridine ring by treatment with approximately one equivalent of an azide salt, such as sodium azide in the presence of approximately one equivalent of an ammonium salt, such as ammonium chloride, in an inert polar solvent, such as dimethylformamide at temperatures of from 50° C. to 125° C., preferably 100° C., for from two to forty-eight hours, preferably twenty-four hours.

Compounds of the formula II and salts thereof may be prepared by reacting a compound of the formula.

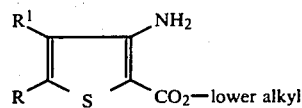

with a compound of the formula

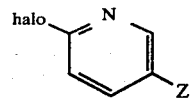

wherein halo, R,R$^1$ and Z are as previously defined. The reaction temperature is from about 130° C. to about 190° C., and reaction time is one-half hour to twenty-four hours, preferably 170° C. to 180° C. for from two to eight hours. The reaction may be run neat or in a high boiling acidic solvent, such as phenol. The ratios of reactants are not critical and approximately equimolar concentrations are employed. This procedure is preferred wherein Z is $CO_2$, $CO_2$-lower alkyl and $CONH_2$.

The starting materials employed in the above process of the formula VIII are either known or readily prepared by reacting a compound of the formula

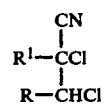

with a lower alkyl mercaptoacetate in the presence of a base.

The starting materials of formula IX are prepared by chlorinating a compound of the formula

using chlorine in the presence of pyridine.

In addition, the compounds of the invention can be prepared using the above procedure wherein Z is cyano and converting the compound of the formula

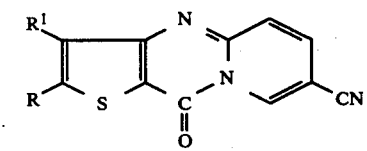

into a compound of the invention by partial hydrolysis employing aqueous strong base and heat followed by acidification to give an amido compound or complete hydrolysis employing aqueous strong acid and heat to give a carboxy compound.

Other methods wherein compounds of the invention can be converted to other compounds of the invention also involve interconversions of the Z group. More specifically, the carboxyl containing compounds of the formula II may be converted to the corresponding esters of the formula II via acid (hydrochloric, benzenesulfonic, etc.) catalysed reactions in inert solvents at temperatures of from about 10° C. to the reflux temperature of the solvent for from fifteen minutes to twenty-four hours.

The reverse of the above procedure, that is the conversion of an ester of formula II to a carboxylic acid of formula II is achieved by carrying out a de-esterification reaction using a strong base, such as sodium hydroxide or potassium hydroxide in an inert polar solvent. The temperature may be from 10° C. to the reflux temperature of the solvent for about fifteen minutes to twenty-four hours followed by adjusting the pH.

A carboxylic acid or ester of formula II can be converted to an amide of formula II by heating in a concentrated solution of ammonia. The reaction may be conducted in an inert polar solvent, such as an alcohol or water using a large excess of ammonia at temperatures of from about 50° C. to the reflux temperature of the solvent for periods of from fifteen minutes to twenty-four hours.

The nitriles of the formula II can be prepared by dehydration of the corresponding amide.

A carboxylic acid of formula II can be converted to a carboxamidotetrazole of formula II by initially converting the carboxylic acid to a reactive intermediate by coupling it with at least one equivalent 1,1'-carbonyldiimidazole or other coupling agent. The reaction takes place in a polar solvent, such as dimethylformamide for from one to sixteen hours at a temperature of from about 40° C. to about 110° C., preferably one hour at 70° C.

The 5-aminotetrazole to be coupled to the above imidazolide is preferably silylated using a silylating agent, such as trimethylchlorosilane and an organic or inorganic base, such as trialkylamine, in a polar solvent, such as dimethylformamide for a period of from thirty minutes to two and one-half hours at from 0° C. to 25° C., preferably one hour at 0° C. to 5° C.

The two components are combined in a polar solvent, such as dimethylformamide, for periods of from four to seventy-two hours at about room temperature to 110° C., preferably fourteen hours at room temperature.

Lastly, the nitrile of formula IX may be converted to tetrazole compounds of the formula II wherein the tetrazole is linked directly to the pyridine ring by treatment with approximately one equivalent of an azide salt, such as sodium azide in the presence of approximately one equivalent of an ammonium salt, such as ammonium chloride, in an inert polar solvent, such as dimethylformamide at temperatures of from 50° C. to 125° C., preferably 100° C., for from two to forty-eight hours, preferably twenty-four hours.

Compounds of the formula III and salts thereof may be prepared by reacting a compound of the formula

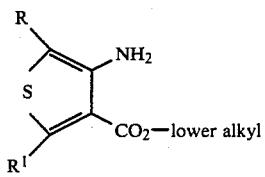

XII with a compound of the formula

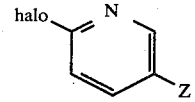

V.

wherein halo, $R,R^1$ and Z are as previously defined. The reaction temperature is from about 130° C. to about 190° C. and reaction time is one-half hour to twenty-four hours, preferably 170° C. to 180° C. for from two to eight hours. The reaction may be run neat or in a high boiling acidic solvent, such as phenol. The ratios of reactants, are not critical and approximately equimolar concentrations are employed. This procedure is preferred wherein Z is $CO_2H$, $CO_2$-lower alkyl and $CONH_2$.

The starting materials employed in the above process of the formula XII are readily prepared by treating a compound of the formula

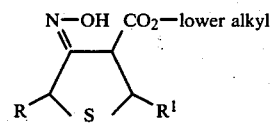

XIII with hydrochloric acid followed by ammonium hydroxide

The compounds of the formula XIII are prepared by treating a compound of the formula

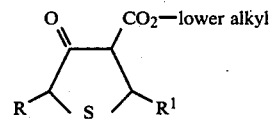

XIV with hydroxylamine.

The compounds of the formula XIV are prepared by reacting a lower alkyl mercaptoacetate with a lower alkyl substituted and unsubstituted, unsaturated carboxylic acid ester in the presence of base.

In addition, the compounds of the invention can be prepared using the above procedure wherein Z is cyano and converting the compound of the formula

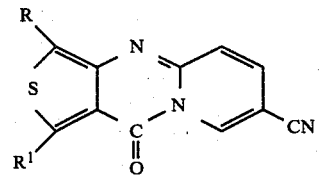

XV into a compound of the invention by partial hydrolysis employing aqueous strong base and heat followed by acidification to give an amide compound or complete hydrolysis employing aqueous strong acid and heat to give a carboxy compound.

Other methods wherein compounds of the invention can be converted to other compounds of the invention also involve interconversions of the Z group. More specifically, the carboxyl containing compounds of the formula III may be converted to the corresponding esters of the formula III via acid (hydrochloric, benzenesulfonic, etc.) catalysed reactions in inert solvents at temperatures of from about 10° C. to the reflux temperature of the solvent for from fifteen minutes to twenty-four hours.

The reverse of the above procedure, that is the conversion of an ester of formula III to a carboxylic acid of formula III is achieved by carrying out a de-esterification reaction using a strong base, such as sodium hydroxide or potassium hydroxide in an inert polar solvent. The temperature may be from 10° C. to the reflux temperature of the solvent for about fifteen minutes to twenty-four hours followed by adjustment of the pH.

A carboxylic acid or ester of formula III can be converted to an amide of formula III by heating in a concentrated solution of ammonia. The reaction may be conducted in an inert polar solvent, such as an alcohol or water using a large excess of ammonia at temperatures of from about 30° C. to the reflux temperature of the solvent for periods of from fifteen minutes to twenty-four hours.

The nitriles of the formula III can be prepared from the corresponding amide by dehydration.

A carboxylic acid of formula III can be converted to a carboxamidotetrazole of formula III by initially converting the carboxylic acid to a reactive intermediate by coupling it with at least one equivalent of 1,1'-carbonyldiimidazole or other coupling agent. The reaction takes place in a polar solvent, such as dimethylformamide for from one to sixteen hours at a temperature of from about 40° C. to about 110° C., preferably one hour at 70° C.

The 5-aminotetrazole to be coupled is preferably silylated using a silylating agent, such as trimethylchlorosilane and an organic or inorganic base, such as trialkylamine. The reaction is conducted in a polar solvent, such as dimethylformamide for a period of from thirty minutes to two and one-half hours at from 0° C. to 25° C., preferably one hour at 0° C. to 5° C.

The two components are combined in a polar solvent, such as dimethylformamide, for periods of from four to seventy-two hours at about room temperature to 110° C., preferably fourteen hours at room temperature.

Lastly, the nitrile intermediate of formula XV may be converted to tetrazole compounds of the formula III wherein the tetrazole is linked directly to the pyridine ring by treatment with approximately one equivalent of an azide salt, such as sodium azide in the presence of approximately one equivalent of an ammonium salt, such as ammonium chloride, in an inert polar solvent, such as dimethylformamide at temperatures of from 50° C. to 125° C., preferably 100° C., for from two to forty-eight hours, preferably twenty-four hours.

Compounds of formula I, II and III and salts thereof can be prepared directly by cyclizing compounds of the formulae

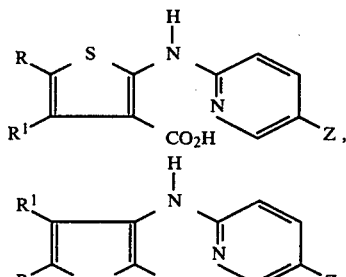

and

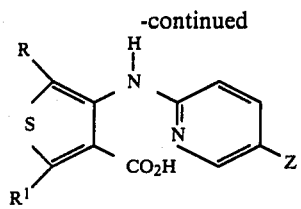

-continued

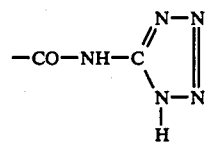

respectively, or their corresponding lower alkyl esters. The compounds wherein Z is —CO$_2$H are prepared in a polar solvent, such as water, containing a large excess of a strong acid, such as hydrochloric acid. The reaction is generally conducted at temperatures of from 20° C. to the refluxing temperature of the solvent for from eight to twenty-four hours, preferably reflux temperature for eighteen hours. The compounds wherein Z is

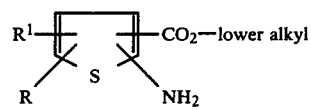

are prepared by the same procedure as given previously for introducing this function onto the already closed ring. The reaction, in one step, closes the ring and introduces the tetrazole group. The silylation step is optional in the foregoing procedure.

While, as shown earlier, the preferred process for preparing compounds of the formulae I to III and salts thereof (except in formula III, R and R$^1$ cannot be bromo, chloro or hydrogen) involves reacting a compound of the formula

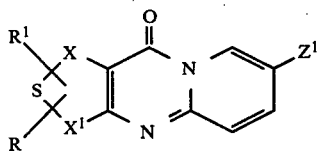

with a compound of the formula V, where R and R$^1$ are as previously defined, another process which is capable of forming compounds of the formulae I to III and salts thereof is the preferred process for preparing compounds of formula III and salts thereof, especially where R and R$^1$ is hydrogen. This preferred process involves the treatment of a novel compound of the formula wherein X is —CH$_2$— and X$^1$ is CH$_2$, X is —CH$_2$CH$_2$— and X$^1$ is a single bond, and X is a single bond and X$^1$ is —CH$_2$CH$_2$— bond; Z$^1$ is CO$_2$ lower alkyl, cyano or a protective derivative of a carboxyl, or groups such as the tri(lower alkyl)silyl derivative and R and R$^1$ are as previously defined, with an N-haloamide, preferably an N-halosuccinimide, wherein halo is bromo or chloro in a basic solvent, preferably pyridine. Approximately equivalent amounts of reactants are employed at temperatures of from about 50° C. to about 120° C., preferably 90° C. to 95° C. The reaction time is not critical and is a function of the temperature; however, generally about 10 minutes to about two hours are employed with a preferred time of twenty minutes.

The starting materials of the formula XX and salts thereof, which are part of the present invention, are prepared by reacting a compound of the formula

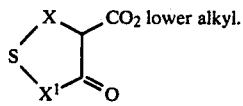 XXI wherein X, X¹, R, R¹ are as previously defined, with a compound of the formula

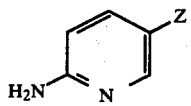 XXII wherein Z is as previously defined, in the presence of an acid catalyst, preferably toluenesulfonic acid or benzenesulfonic acid.

This reaction is generally run neat although this is not essential with about two equivalents of compound XXI for each equivalent of compound XXII. The reaction is carried out at about 160° C. to about 185° C., preferably 170° C. for from about 30 minutes to about 24 hours, preferably about one to two hours.

Starting materials of the formula XXII are generally known or prepared from the readily available compound where Z is carboxyl by methods described earlier for interconverting the functional group on compounds of the invention. The starting material of the formula XXI wherein X and X¹ is —CH₂— and R and R¹ are as previously described are prepared by treating a compound of the formula

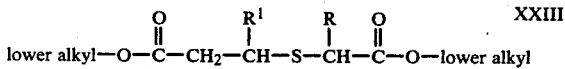 XXIII with sodium methoxide in a methanolic solvent.

Compounds of the formula XXIII are prepared by reacting a compound of the formula

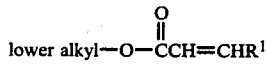 XXIV with a compound of the formula

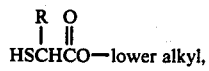 XXV in the presence of piperidine

Starting materials of the formula XXI wherein X is —CH₂CH₂— and X¹ is a single bond and R and R¹ are as previously described are prepared by a literature procedure reported in Rec. Trav. Chim. Pays - Bas 96 (6) (1977)161 which is incorporated by reference.

Starting materials of the formula XXI where X is a single bond and X¹ is —CH₂CH₂— and R and R¹ are as previously described are usually employed in a semi-pure state with a contaminant of the formula

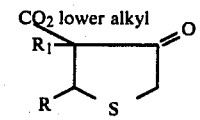 XXVI

This contaminant may be removed by chromatography at any desirable stage.

The above starting material having the formula

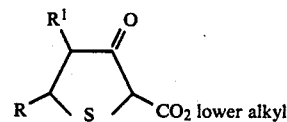 XXIa is prepared by cyclizing a compound of the formula

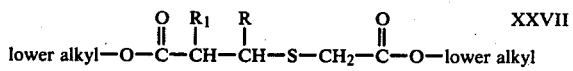 XXVII using sodium methoxide.

The compounds of the formula XXVII are prepared by reacting a compound of the formula

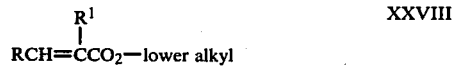 XXVIII with a compound of the formula

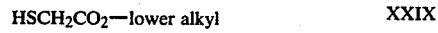 XXIX in the presence of piperidine

Lastly compounds of the invention wherein R or R¹ is chloro or bromo are prepared from a compound of formula XX wherein R and R¹ are hydrogen, lower alkyl, phenyl or X-substituted phenyl where X is as previously defined with the proviso that when R is a group other than hydrogen, R¹ is hydrogen and when R¹ is a group other than hydrogen, R is hydrogen by a direct halogenation procedure.

The process employs a trialkylchlorosilane, pyridine and an excess of N-halosuccinimide where halo is chloro or bromo. The process is carried out using the same conditions used to prepare compounds of the formula I to III.

The compounds of this invention are useful pharmacological agents. More specifically, the compounds are useful in the treatment of allergies, such as asthma, hay fever, rhinitis, and other allergic conditions.

The compounds may be administered orally, parenterally, rectally, or by inhalation therapy. The usual mammalian dosage such as for dogs, cats, etc., range for a 70 kg subject from about 7 mg to about 1 g per day (0.1 mg to 15 mg per kg of weight per day), preferably 21 mg to 350 mg per day (0.3 mg to 5 mg per kg of weight per day), optionally in divided portions.

The above employed pharmaceutical compositions are produced by formulating a compound of the foregoing formula (active ingredient) in dosage unit form with a pharmaceutical carrier. Some examples of dosage unit forms are tablets, capsules, lozenges, and pills; as well as powders and aqueous and non-aqueous oral solutions and suspensions and parenteral solutions, nose drops or sprays and inhalation aerosols, packaged in containers containing either one or some larger number of dosage units and capable of being subdivided into individual doses by such means as measurement into a teaspoon or other standard container. Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc, stearic acid; magnesium stearate; vegetable oils such as peanut oil, cottonseed oil, sesame oil, olive oil, corn oil, and oil of theobroma; propylene glycol; glycerine, sorbitol; polyethylene glycol; water; agar; alginic acid; isotonic saline, and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents, and where the pharmaceutical is part of a spray inhaler, it may contain non-toxic propellants.

The percentage of the active ingredient in the foregoing compositions can be varied within wide limits but for practical purposes it is preferably present in a concentration of at least 10% in a solid composition and at least 2% in a primarily liquid composition. The most satisfactory compositions are those in which a much higher proportion of the active ingredient is present. The compositions of the invention preferably contain from 2 mg. to 1.0 g of the active ingredient per dosage unit so that the entire amount to be administered during a day can be made up from a reasonable number of dosage units.

The anti-allergic activity of the compounds of this invention has been determined using the passive cutaneous anaphylaxis (PCA) test as described in Immunopharmacology, ed. M. E. Rosenthale and H. C. Mansmann, John Wiley and Son, N.Y., U.S.A., 1975, pages 103-124 and U.S. Pat. No. 4,056,532. The activity of most of the preferred compounds is given in the accompanying table.

In addition, compounds of formula I to III are useful as intermediates in forming other compounds of formulae I to III as shown above.

The invention is further illustrated by the following examples.

ACTIVITY IN PCA TEST

| COMPOUND | PCA TEST I.V. % Inhibition | Dose mg/kg | I.P. % Inhibition | Dose mg/kg | P.O. % Inhibition | Dose mg/kg |
|---|---|---|---|---|---|---|
| 2-Methyl-4-oxo-4H-pyrido[1,2-a]thieno[2,3-d]pyrimidine-7-carboxylic acid | N | 0.1 | 100 | 5 | 62 | 5 |
|  |  |  |  |  | N | 1 |
|  | 33 | 0.1 | 100 | 5 | 100 | 5 |
|  | N | 0.01 |  |  | 100 | 2.5 |
| 2-Ethyl-4-oxo-4H-pyrido[1,2-a]thieno[2,3-d]pyrimidine-7-carboxylic acid |  |  |  |  | 67 | 1.0 |
|  |  |  |  |  | 69 | 0.5 |
|  |  |  |  |  | N | 0.1 |
| 2-Ethyl-4-oxo-4H-pyrido[1,2-a]thieno[2,3-d]pyrimidine-7-carboxylic acid, methyl ester |  |  | 100 | 5 | 75 | 5 |
| 4-oxo-2-propyl-4H-pyrido[1,2-a]thieno[2,3-d]pyrimidine-7-carboxylic acid | N | 0.1 | 68 | 5 | 80 | 5 |
|  |  |  |  |  | 18 | 1.0 |
|  |  |  |  |  | N | 0.1 |
| 2,3-Dimethyl-4-oxo-N-1H-tetrazol-5-yl-4H-pyrido-[1,2-a]-thieno[2,3-d]-pyrimidine-7-carboxamide | 23 | 0.1 | 94 | 5 | N | 5 |
|  | 18 | 0.01 |  |  |  |  |
| 2-Methyl-4-oxo-4H-pyrido[1,2-a]thiene[2,3-d]pyrimidine-7-carboxamide |  |  | 100 | 5 | 38 | 5 |
|  |  |  | 88 | 5 | 100 | 5 |
| 2-Methyl-4-oxo-4H-pyrido[1,2-a]thieno[2,3-d]pyrimidine-7-carbonitrile |  |  |  |  | 12 | 1 |
|  |  |  |  |  | N | 0.5 |
| 2-Methyl-7-(1H-tetrazol-5-yl)-4H-pyrido[1,2-a]thieno[2,3-d]pyrimidine-4-one | 18 | 0.1 | 100 | 5 | N | 5 |
|  | N | 0.01 |  |  |  |  |
|  | 56 | 0.1 | 97 | 5 | 100 | 5 |
|  | N | 0.05 |  |  | 72 | 1 |
| 2-Ethyl-7-(1H-tetrazol-5-yl)-4H-pyrido[1,2-a]thieno[2,3-d]pyrimidin-4-one |  |  |  |  | 51 | 1 |
|  |  |  |  |  | 38 | 0.5 |
|  |  |  |  |  | 36 | 0.5 |
| 2-Propyl-7-(1H-tetrazol-5-yl)-4H-pyrido[1,2-a]thieno[2,3-d]-pyrimidin-4-one |  |  | 100 | 5 | 67 | 5 |
| 2-Phenyl-7-(1H-tetrazol-5-yl)-4H-pyrido[1,2-a]thieno[2,3-d]pyrimidin-4-one |  |  | 84 | 5 | N | 5 |
| 2-(1-Methylethyl)-4-oxo-4H-pyrido[1,2-a]thieno[2,3-d]pyrimidine-7-carboxamide |  |  | 100 | 5 |  |  |
| 2-(1-Methylethyl)-4-oxo-4H-pyrido[1,2-a]thieno[2,3-d]pyrimidine-7-carboxylic acid |  |  | 100 | 5 |  |  |
| 2-Methyl-7-(1H-tetrazol-5-yl)-10H-pyrido[1,2-a]thieno[3,2-d]pyrimidin-10-one |  |  | 51 | 5 |  |  |
| 2-Methyl-10-oxo-10H-pyrido[1,2-a]thieno[3,2-d]pyrimidine-7-carboxylic acid |  |  | 61 | 5 | 41 | 5 |
| 10-oxo-1H-tetrazol-5-yl-10H-pyrido[1,2-a]thieno[3,2-d]pyrimidine-7-carboxamide |  |  | 100 | 5 |  |  |
| 1,3-Dimethyl-10-oxo-10H-pyrido[1,2-a]thieno[3,4-d]pyrimidine-7-carboxylic acid |  |  | 70 | 5 |  |  |
| 7-(1H-Tetrazol-5-yl)-10H-pyrido[1,2-a]thieno[3,4-d]pyrimidine-10-one |  |  | 100 | 5 |  |  |
| 3,10-Dihydro-10-oxo-7-(1H-tetrazol-5-yl)-1H-pyrido[1,2-a]thieno-[3,1-d]pyrimidine |  |  | 100 | 5 |  |  |

N is level where no significant activity was shown
blank space indicates no test was conducted.

EXAMPLE 1

2-Methyl-4-oxo-4H-pyrido[1,2-a]thieno[2,3-d]pyrimidine-7-carboxylic acid

A mixture of 2-amino-5-methyl-3-thiophenecarboxylic acid, ethyl ester (*Chemische Berichte*, Vol. 99, page 94–100, 1966), 18.5 g (0.1 mol) and 6-chloro-3-pyridinecarboxylic acid (Aldrich Chemical Company), 15.7 g (0.1 mol) is heated in an oil bath at 170°–190° C. for 20 hours. The mixture is cooled, extracted with hot chloroform and the residue is dissolved in hot pyridine, cooled and 0.4 g of 2-methyl-4-oxo-4H-pyrido[1,2-a]thieno[2,3-d]pyrimidine-7-carboxylic acid is collected; mp 312°–315° C. after recrystallization from methanol.

EXAMPLE 2

2-Ethyl-4-oxo-4H-pyrido[1,2-a]thieno[2,3-d]pyrimidine-7-carboxylic acid

A mixture of 2-amino-5-ethyl-3-thiophenecarboxylic acid, ethyl ester (*Chemische Berichte*, Vol. 99, pages 94–100, 1966), 2.0 g (0.01 mol) and 6-chloro-3-pyridinecarboxylic acid (Aldrich Chemical Company), 1.6 g (0.01 mol) is heated in an oil bath at 180°–185° C. for six hours. The mixture is cooled, dissolved in hot glacial acetic acid, activated charcoal (Darco G-60, Matheson, Coleman and Bell) added and the hot suspension filtered through Supercell Hyflo ® (Johns-Manville). The filtrate is cooled and 0.33 g of 2-ethyl-4-oxo-4H-pyrido[1,2-a]thieno-[2,3-d]pyrimidine-7-carboxylic acid is collected; mp 255°–257° C. after recrystallization from methanol.

EXAMPLE 3

4-Oxo-2-propyl-4H-pyrido[1,2-a]thieno[2,3-d]pyrimidine-7-carboxylic acid

A mixture of 2-amino-5-propyl-3-thiophenecarboxylic acid, ethyl ester, 7.4 g (0.035 mol) and 6-chloro-3-pyridinecarboxylic acid (Aldrich Chemical Company), 6.4 g (0.041 mol) is heated in an oil bath at 180° C. for two hours. The mixture is cooled, extracted with hot chloroform and the residue is dissolved in hot pyridine, cooled and 0.45 g of 4-oxo-2-propyl-4H-pyrido[1,2-a]thieno[2,3-d]pyrimidine-7-carboxylic acid is collected; mp 250°–254° C. after recrystallization from pyridine.

EXAMPLE 4

2-Butyl-4-oxo-4H-pyrido[1,2-a]thieno[2,3-d]pyrimidine-7-carboxylic acid

A mixture of 2-amino-5-butyl-3-thiophenecarboxylic acid, methyl ester, 21.33 g (0.1 mol) and 6-chloro-3-pyridinecarboxylic acid (Aldrich Chemical Company), 15.76 g (0.1 mol) is heated in a wax bath at 178°–180° C. for one hundred ninety minutes. The mixture is cooled, extracted with hot chloroform and the residue is dissolved in 300 ml of hot glacial acetic acid filtered and 600 ml of hot water added and the mixture stirred on a steam bath for forty minutes and filtered to give 1.23 g of 2-butyl-4-oxo-4H-pyrido[1,2-a]thieno[2,3-d]pyrimidine-7-carboxylic acid; mp 250°–252° C. after recrystallization from pyridine.

EXAMPLE 5

4-Oxo-B 2-phenyl-4H-pyrido[1,2-a]thieno[2,3-d]pyrimidine-7-carboxylic acid

From 5.0 g (0.02 mol) of 2-amino-5-phenyl-3-thiophenecarboxylic acid, ethyl ester (Chemische Berichte, Vol. 99, pages 94–100, 1966) and 3.2 g (0.02 mol) of 6-chloro-3-pyridinecarboxylic acid (Aldrich Chemical Company), following the procedure of Example 3, there is obtained 0.4 g of 4-oxo-2-phenyl-4H-pyrido[1,2-a]thieno [2,3-d]pyrimidine-7-carboxylic acid; mp 387°–392° C. after recrystallization from pyridine.

EXAMPLE 6

2,3-Dimethyl-4-oxo-4H-pyrido[1,2-a]thieno[2,3-d]pyrimidine-7-carboxylic acid

From 8.0 g (0.04 mol) of 2-amino-4,5-dimethyl-3-thiophenecarboxylic acid, ethyl ester (*Chemische Berichte*, Vol. 99, pages 94–100, 1966) and 6.3 g (0.04 mol) of 6-chloro-3-pyridinecarboxylic acid (Aldrich Chemical Company) following the procedure of Example 3, there is obtained 0.2 g of 2,3-dimethyl-4-oxo-4H-pyrido[1,2-a]thieno[2,3-d]pyrimidine-7-carboxylic acid; mp 364°–368° C. after recrystallization from pyridine.

EXAMPLE 7

2-Ethyl-4-oxo-4H-pyrido[1,2-a]thieno[2,3-d]pyrimidine-7-carboxylic acid, methyl ester A mixture of 10 g (0.05 mol) of 2-amino-5-ethyl-3-thiophenecarboxylic acid, ethyl ester (*Chemische Berichte*, Vol. 99, pages 94–100, 1966) and 8.61 g (0.05 mol) of 6-chloro-3-pyridinecarboxylic acid, methyl ester (*Alfred Bader Chemical Company*) is heated in a wax bath at 178°–188° C. for three hours under nitrogen. The distillate is collected in a Dean-Stark trap attached to the reaction flask. The mixture is cooled, dissolved in hot methanol, cooled and 5.5 g of 2-ethyl-4-oxo-4H-pyrido[1,2-a]thieno[2,3-d]pyrimidine-7-carboxylic acid, methyl ester is collected; mp 151°–152° C. after recrystallization from methanol.

EXAMPLE 8

2-Butyl-4-oxo-4H-pyrido[1,2-a]thieno[2,3-d]pyrimidine-7-carboxylic acid, methyl ester From 5.1 g (0.024 mol) of 2-amino-5-butyl-3-thiophenecarboxylic acid, methyl ester and 4.1 g (0.024 mol) of 6-chloro-3-pyridinecarboxylic acid, methyl ester (Alfred Bader Chemical Company), following the procedure of Example 7, there is obtained 3.2 g of 2-butyl-4-oxo-4H-pyrido[1,2-a]thieno[2,3-d]pyrimidine-7-carboxylic acid, methyl ester; mp 137°–138° C. after recrystallization from methanol.

EXAMPLE 9

2-Methyl-4-oxo-N-1H-tetrazol-5-yl-4H-pyrido[1,2-a]thieno[2,3-d]-pyrimidine-7-carboxamide 1.86 g (0.00715 mol) of 2-methyl-4-oxo-4H-pyrido[1,2-a]thieno[2,3-d]pyrimidine-7-carboxylic acid (Example 1) and 1.62 g (0.01 mol) of 1,1′carbonyldiimidazole (Aldrich Chemical Company) in 210 ml of dimethylformamide are stirred at 50° C. for sixteen hours. To 0.83 g (0.008 mol) of 5-aminotetrazole monohydrate (Aldrich Chemical Company) in 50 ml of dimethylformamide cooled to 0°–5° C. is added 3.0 ml (0.024 mol) of chlorotrimethylsilane (Aldrich Chemical Company) and 6.0 ml (0.043 mol) of triethylamine. After thirty minutes the mixture is allowed to reach room temperature and is stirred for an additional two hours. This mixture is combined with the previous cooled imidazolide mixture and stirred for three days at room temperature. The resulting precipitate is collected, slurried in boiling glacial acetic acid, the mixture is cooled and filtered to give 0.69 g of 2-methyl-4-oxo-N-1H-tetrazol-5-yl-4H-pyrido[1,2-a]thieno[2,3-d]pyrimidine-7-carboxamide; mp 306°–310° C. (dec).

EXAMPLE 10

2-Ethyl-4-oxo-N-1H-tetrazol-5-yl-4H-pyrido[1,2-a]thieno[2,3-d]-pyrimidine-7-carboxamide 0.64 g (0.0023 mol) of 2-ethyl-4-oxo-4H-pyrido[1,2-a]thieno-[2,3-d]pyrimidine-7-carboxylic acid (Example 2) and 0.75 g (0.0046 mol) of 1,1'carbonyldiimidazole (Aldrich Chemical Company) in 70 ml of dimethylformamide are stirred at 70° C. for two and one-half hours. To 0.31 g (0.003 mol) of 5-aminotetrazole monohydrate (Aldrich Chemical Company) in 40 ml of dimethylformamide cooled to 0°–5° C. is added 1.5 ml (0.012 mol) of chlorotrimethylsilane (Aldrich Chemical Company) and 2.5 ml (0.018 mol) of triethylamine. The mixture is stirred and allowed to reach room temperature. After two hours the mixture is combined with the previous imidazolide mixture and stirred for fourteen hours at room temperature. The resulting precipitate is collected, slurried in boiling glacial acetic acid, the mixture is cooled and filtered to give 0.58 g of 2-ethyl-4-oxo-N-1H-tetrazol-5-yl-4H-pyrido[1,2-a]thieno[2,3-d]pyrimidine-7-carboxamide; mp 310°–312° C. (dec).

EXAMPLE 11

4-Oxo-2-propyl-N-1H-tetrazol-5-yl-4H-pyrido[1,2-a]thieno[2,3-d]-pyrimidine-7-carboxamide 5.77 g (0.02 mol) of 4-oxo-2-propyl-4H-pyrido[1,2-a]thieno[2,3-d]-pyrimidine-7-carboxylic acid (Example 3) and 6.49 g (0.04 mol) of 1,1'carbonyldiimidazole (Aldrich Chemical Company) in 100 ml of dimethylformamide are stirred at 50° C. for one hour. To 2.5 g (0.024 mol) of 5-aminotetrazole monohydrate (Aldrich Chemical Company) in 50 ml of dimethylformamide cooled to 0°–5° C. is added 9.14 ml (0.072 mol) of chlorotrimethylsilane (Aldrich Chemical Company) and 10 ml (0.072 mol) of triethylamine. The mixture is stirred and allowed to reach room temperature. After two hours the mixture is combined with the previous imidazolide mixture and stirred for fourteen hours at room temperature. The resulting precipitate 0.9 g, of 4-oxo-2-propyl-N-1H-tetrazol-5-yl-4H-pyrido[1,2-a]thieno[2,3-d]pyrimidine-7-carboxamide is collected; mp 306°–308° C. (dec) after recrystallization from pyridine.

EXAMPLE 12

2-Butyl-4-oxo-N-1H-tetrazol-5-yl-4H-pyrido[1,2-a]thieno[2,3-d]-pyrimidine-7-carboxamide 1.6 g (0.0053 mol) of 2-butyl-4-oxo-4H-pyrido[1,2-a]thieno[2,3-d]-pyrimidine-7-carboxylic acid (Example 4) and 1.75 g (0.0108 mol) of 1,1' carbonyldiimidazole (Aldrich Chemical Company) in 50 ml of dimethylformamide are stirred under a nitrogen atmosphere at 105° C. for seventy minutes. The mixture is allowed to stand at room temperature for thirty minutes and then 0.545 g (0.00529 mol) of 5-aminotetrazole monohydrate (Aldrich Chemical Company) is added and the mixture heated at 105° C. for one hundred minutes. The solvent is evaporated and the residue is dissolved in dimethylformamide and filtered. The filtrate is cooled and 1.1 g of 2-butyl-4-oxo-N-1H-tetrazol-5-yl-4H-pyrido[1,2-a]thieno[2,3-d]-pyrimidine-7-carboxamide is collected; mp 290° (dec).

EXAMPLE 13

4-Oxo-2-phenyl-N-1H-tetrazol-5-yl-4H-pyrido[1,2-a]thieno[2,3-d]-pyrimidine-7-carboxamide 0.9 g (0.0028 mol) of 4-oxo-2-phenyl-4H-pyrido[1,2-a]thieno[2,3-d]-pyrimidine-7-carboxylic acid (Example 5) and 0.7 g (0.0043 mol) of 1,1'carbonyldiimidazole (Aldrich Chemical Company) in 80 ml of dimethylformamide are stirred at 60°–70° C. for five hours. To 0.4 g (0.004 mol) of 5-aminotetrazole monohydrate (Aldrich Chemical Compay) is 40 ml of dimethylformamide cooled to 0°–5° C. is added 1.5 ml (0.012 mol) of chlorotrimethylsilane (Aldrich Chemical Company) and 3 ml (0.022 mol) of triethylamine. After thirty minutes the mixture is allowed to reach room temperature and is stirred for an additional two hours. The mixture is combined with the previous imidazolide mixture and stirred for fourteen hours at room temperature. The resulting precipitate is collected, slurried in boiling glacial acetic acid, and mixture is cooled and filtered to give 0.78 g of 4-oxo-2-phenyl-N-1H-tetrazol-5-yl-4H-pyrido[1,2-a]thieno[2,3-d]pyrimidine-7-carboxamide; mp 324°–328° C. (dec).

EXAMPLE 14

2,3-Dimethyl-4-oxo-N-1H-tetrazol-5-yl-4H-pyrido[1,2-a]thieno-[2,3-d]-pyrimidine-7-carboxamide From 1 g (0.0036 mol) of 2,3-dimethyl-4-oxo-4H-pyrido[1,2-a]-thieno[2,3-d]pyrimidine-7-carboxylic acid (Example 6), 0.83 g (0.0051 mol) of 1,1'carbonyldiimidazole (Aldrich Chemical Company) in 50 ml of dimethylformamide and 0.41 g (0.004 mol) of 5-aminotetrazole monohydrate (Aldrich Chemical Company), 1.5 ml (0.012 mol) of chlorotrimethylsilane (Aldrich Chemical Company), 3.0 ml (0.022 mol) of triethylamine in 40 ml of dimethylformamide, following the procedure of Example 11, there is obtained 0.73 g of 2,3-dimethyl-4-oxo-N-1H-tetrazol-5-yl-4H-pyrido[1,2-a]thieno-[2,3-d]pyrimidine-7-carboxamide after slurrying in boiling glacial acetic acid, cooling and filtering the precipitate; mp 297°–300° C. (dec).

EXAMPLE 15

2-(1-Methylethyl)-4-oxo-4H-pyrido[1,2-a]thieno[2,3-d]pyrimidine-7-carboxamide

A mixture of 24.0 g (0.1538 mol) of 6-chloro-3-pyridine-carboxamide (Aldrich Chemical Company) and 32.8 g (0.1538 mol) of 2-amino-5-(1-methylethyl)-3-thiophenecarboxylic acid, ethyl ester (*Tetrahedron*, Vol. 33, pages 2089–2092, 1977) is heated in a wax bath at 178°–182° C. for two hundred five minutes and then at 180°–196° C. for sixty-five minutes under nitrogen. The mixture is cooled, suspended in hot methanol and filtered to give 8.9 g of 2-(1-methylethyl)-4-oxo-4H-pyrido[1,2-a]thieno[2,3-d]pyrimidine 7-carboxamide; mp 280°–282° C. after recrystallization from dimetylformamide.

EXAMPLE 16

2-(1-Methylethyl)-4-oxo-4H-pyrido[1,2-a]thieno[2,3-d]pyrimidine-7-carbonitrile 2-(1-Methylethyl)-4-oxo-4H-pyrido[1,2-a]thieno[2,3-d]pyrimidine-7-carboxamide (Example 15), 8.7 g (0.0303 mol), in 250 ml of phosphorus oxychloride and 250 ml of chloroform is refluxed on a steam bath for four hours under nitrogen. The chloroform and excess phosphorus oxychloride are evaporated in vacuo and the residue is treated with 2 L of ice water. The resulting precipitate is filtered to give 5.3 g of 2-(1-methylethyl)-4-oxo-4H-pyrido[1,2-a]thieno[2,3-d]pyrimidine-7-carbonitrile; mp 225°-226° C. after recrystallization from pyridine.

EXAMPLE 17

2-(1-Methylethyl)-7-(1H-tetrazol-5-yl)-4H-pyrido[1,2-a]thieno-[2,3-d]pyrimidin-4-one A mixture of 5.1 g (0.01894 mol) of 2-(1-methylethyl)-4-oxo-4H-pyrido[1,2-a]thieno[2,3-d]pyrimidine-7-carbonitrile (Example 16), 6.5 g (0.1 mol ) of sodium azide and 5.35 g (0.1 mol) of ammonium chloride in 150 ml of dimethylformamide is stirred and heated at 124° C. for twenty-two hours under nitrogen. The reaction mixture is cooled, filtered and the filtrate evaporated. The residue is treated with 1 1 water and acidified with concentrated hydrochloric acid. The resulting precipitate is collected, suspended in hot water, the suspension cooled and filtered to give 3.3 g of 2-(1-methylethyl)-7-(1H-tetrazol-5-yl)-4H-pyrido-[1,2-a]thieno[2,3-d]pyrimidin-4-one; mp 288° C. (dec) after recrystallization from pyridine-ethanol.

EXAMPLE 18

2-(1-Methylethyl)-4-oxo-4H-pyrido[1,2-a]thieno[2,3-d]pyrimidine-7-carboxylic acid A mixture of 21.33 g (0.1 mol) of 2-amino-5-(1-methylethyl)-3-thiophenecarboxylic acid, ethyl ester (*Tetrahedron*, Vol. 33, pages 2089–2092, 1977) and 17.16 g (0.1 mol) of 6-chloro-3-pyridinecarboxylic acid, methyl ester (Alfred Bader Chemical Company) is heated in a wax bath at 178°-182° C. for one hundred eighty-seven minutes and then at 182°-205° C. for ninety minutes under nitrogen. The distillate is collected in a Dean-Stark Trap attached to the reaction flask. The mixture is cooled, dissolved in methanol, cooled and 16.2 g of a mixture of 2-(1-methylethyl)-4-oxo-4H-pyrido[1,2-a]thieno[2,3-d]pyrimidine-7-carboxylic acid, methyl ester and the ring-opened diester, 6-[[3-(ethoxycarbonyl)-5-(1-methylethyl)-2-thienyl]amino]-3-pyridinecarboxylic acid, methyl ester, is collected; mp 112°-114° C. A suspension of 11 g of the previous mixture in 250 ml of concentrated hydrochloric acid and 250 ml of water is refluxed in a wax bath at 142° C. for twenty-two hours under nitrogen. The suspension is cooled to room temperature, filtered and the precipitate washed with 300 ml of water and dried to give 6.0 g of 2-(1-methylethyl)-4-oxo-4H-pyrido[1,2-a]thieno[2,3-d]pyrimidine-7-carboxylic acid; mp 264°-266° C. after recrystallization from ethanol.

EXAMPLE 19

2-(1-Methylethyl)-4-oxo-4H-pyrido[1,2-a]thieno[2,3-d]pyrimidine-7-carboxylic acid, ethyl ester A cooled suspension of 1.4 g (0.00486 mol) of 2-(1-methylethyl)-4-oxo-4H-pyrido[1,2-a]thieno[2,3-d]pyrimidin-7-carboxylic acid (Example 18) in 150 ml of ethanol is saturated with hydrogen chloride. The mixture is stirred and refluxed in a wax bath at 128° C. for eighteen hours under nitrogen. The ethanol is evaporated in vacuo to give 0.43 g of 2-(1-methylethyl)-4-oxo-4H-pyrido[1,2-a]thieno[2,3-d]pyrimidine-7-carboxylic acid, ethyl ester; mp 122°-123° C. after recrystallization from absolute ethanol.

EXAMPLE 20

2-(1-Methylethyl)-4-oxo-N-1H-tetrazol-5-yl-4H-pyrido[1,2-a]-thieno[2,3-d]pyrimidine-7-carboxamide 2.88 g (0.01 mol) of 2-(1-methylethyl)-4-oxo-4H-pyrido[1,2-a]-thieno[2,3-d]pyrimidin-7-carboxylic acid (Example 18) and 3.31 g (0.02 mol) of 1,1' carbonyldiimidazole (Aldrich Chemical Company) in 100 ml of dimethylformamide are stirred and heated in a wax bath at 105° C. for ninety minutes under nitrogen. The mixture is cooled and stirred at room temperature for thirty minutes and 1.03 g (0.01 mol) of 5-aminotetrazole monohydrate (Aldrich Chemical Company) is added and the resulting mixture is stirred and heated at 105° C. for one hundred thirty-five minutes under nitrogen. The mixture is allowed to stand overnight at room temperature, the precipitate is filtered and the filtrate is evaporated in vacuo. The residue is slurried in boiling methanol, the mixture cooled and filtered. This precipitate is combined with the previous precipitate to give 1.8 g of 2-(1-methylethyl)-4-oxo-N-1H-tetrazol-5-yl-4H-pyrido[1,2-a]-thieno[2,3-d]pyrimidine-7-carboxamide; mp 307° C. (dec) after recrystallization from pyridine.

EXAMPLE 21

2-Methyl-4-oxo-4H-pyrido[1,2-a]thieno[2,3-d]pyrimidine-7-carboxamide

A mixture of 6.0 g (0.038 mol) of 6-chloro-3-pyridinecarboxamide (Aldrich Chemical Company) and 10.0 g (0.054 mol) of 2-amino-3-methyl-3-thiophenecarboxylic acid, ethyl ester (*Chemische Berichte*, Vol. 99, pages 94–100, 1966) is heated in an oil bath at 185° C. for one hour then at 135°-140° C. for sixteen hours and finally at 195° C. for six hours. The mixture is cooled and then suspended in hot chloroform and filtered to give 0.6 g of 2-methyl-4-oxo-4H-pyrido[1,2-a]thieno[2,3-d]pyrimidine-7-carboxamide; mp 350°-354° C. after recrystallization from pyridine.

EXAMPLE 22

2-Ethyl-4-oxo-4H-pyrido[1,2-a]thieno[2,3-d]pyrimidine-7-carboxamide

A mixture of 6.0 g (0.038 mol) of 6-chloro-3-pyridinecarboxamide (Aldrich Chemical Company) and 8.0 g (0.040 mol) of 2-amino-5-ethyl-3-thiophenecarboxylic acid, ethyl ester (*Chemische Berichte*, Vol. 99, pages 94–100, 1966) is heated in an oil bath at 180° C. for two hours. The mixture is cooled and then suspended in hot chloroform and filtered to give 1.8 g of 2-ethyl-4-oxo-4H-pyrido-[1,2-a]thieno[2,3-d]pyrimidine-7-carboxamide; mp 278°-280° C. after recrystallization from pyridine.

EXAMPLE 23

4-Oxo-2-propyl-4H-pyrido[1,2-a]thieno[2,3-d]pyrimidine-7-carboxamide

From 4.6 g (0.0029 mol) of 6-chloro-3-pyridinecarboxamide (Aldrich Chemical Company) and 8.6 g (0.040 mol) of 2-amino-5-propyl-3-thiophenecarboxylic acid, ethyl ester, following the procedure of Example 22 there is obtained 2.6 g of 4-oxo-2-propyl-4H-pyrido[1,2-a]thieno[2,3-d]pyrimidine-7-carboxamide; mp 260°–264° C. after recrystallization from pyridine.

EXAMPLE 24

2-Butyl-4-oxo-4H-pyrido[1,2-a]thieno[2,3-d]pyrimidine-7-carboxamide

From 6.2 g (0.040 mol) of 6-chloro-3-pyridinecarboxamide (Aldrich Chemical Company) and 9.0 g (0.040 mol) of 2-amino-5-butyl-3-thiophenecarboxylic acid, ethyl ester and heating in a wax bath at 180°–195° C. for one hundred forty-five minutes and then at 185°–200° C. for ninety minutes, following the procedure of Example 22 there is obtained 1.9 g of 2-butyl-4-oxo-4H-pyrido-[1,2-a]thieno[2,3-d]pyrimidine-7-carboxamide; mp 266°–267° C. after recrystallization from glacial acetic acid.

EXAMPLE 25

4-Oxo-2-phenyl-4H-pyrido[1,2-a]thieno[2,3-d]pyrimidine-7-carboxamide, monoacetate From 4.7 g (0.030 mol) of 6-chloro-3-pyridinecarboxamide (Aldrich Chemical Company) and 7.5 g (0.030 mol) of 2-amino-5-phenyl-3-thiophenecarboxylic acid, ethyl ester (*Chemische Berichte*, Vol. 99, pages 94–100, 1966), following the procedure of Example 22, there is obtained 0.4 g of 4-oxo-2-phenyl-4H-pyrido[1,2-a]thieno[2,3-d]pyrimidine-7-carboxamide, monoacetate; mp 348°–352° C. after recrystallization from glacial acetic acid.

EXAMPLE 26

2,3-Dimethyl-4-oxo-4H-pyrido[1,2-a]thieno[2,3-d]pyrimidine-7-carboxamide

From 6.0 g (0.038 mol) of 6-chloro-3-pyridinecarboxamide (Aldrich Chemical Company) and 8.0 g (0.040 mol) of 2-amino-4,5-dimethyl-3-thiophenecarboxylic acid, ethyl ester (*Chemische Berichte*, Vol. 99, pages 94–100, 1966), following the procedure of Example 22, there is obtained 2,3-dimethyl-4-oxo-4H-pyrido[1,2-a]thieno-[2,3-d]pyrimidine-7-carboxamide; mp 361°–363° C. after recrystallization from pyridine.

EXAMPLE 27

2-Methyl-4-oxo-4H-pyrido[1,2-a]thieno[2,3-d]pyrimidine-7-carbonitrile

2-Methyl-4-oxo-4H-pyrido[1,2-a]thieno[2,3-d]pyrimidine-7-carboxamide (Example 21), 2.6 g (0.010 mol), in 30 ml of phosphorus oxychloride and 30 ml of chloroform is refluxed on a steam bath for three hours. The chloroform and excess phosphorus oxychloride are evaporated in vacuo and the residue is treated with 200 ml of ice water. The resulting precipitate is filtered to give 2.1 g of 2-methyl-4-oxo-4H-pyrido[1,2-a]-thieno[2,3-d]pyrimidine-7-carbonitrile; mp 256°–258° C. after recrystallization from glacial acetic acid.

EXAMPLE 28

2-Ethyl-4-oxo-4H-pyrido[1,2-a]thieno[2,3-d]pyrimidine-7-carbonitrile

From 1.3 g (0.0048 mol) of 2-ethyl-4-oxo-4H-pyrido[1,2-a]-thieno[2,3-d]pyrimidine-7-carboxamide (Example 22), 30 ml of phosphorus oxychloride and 30 ml of chloroform and refluxing on a steam bath for six hours, following the procedure of Example 27, there is obtained 1.18 g of 2-ethyl-4-oxo-4H-pyrido[1,2-a]-thieno[2,3-d]pyrimidine-7-carbonitrile; mp 223°–224° C. after recrystallization from glacial acetic acid.

EXAMPLE 29

4-oxo-2-propyl-4H-pyrido[1,2-a]thieno[2,3-d]pyrimidine-7-carbonitrile

From 2.0 g (0.007 mol) of 4-oxo-2-propyl-4H-pyrido[1,2-a]thieno-[2,3-d]pyrimidine-7-carboxamide (Example 23), 30 ml of phosphorus oxychloride and 30 ml of chloroform, following the procedure of Example 27, there is obtained 1.8 g of 4-oxo-2-propyl-4H-pyrido-[1,2-a]thieno[2,3-d]pyrimidine-7-carbonitrile; mp 217°–218° C. after recrystallization from glacial acetic acid.

EXAMPLE 30

2-Butyl-4-oxo-4H-pyrido[1,2-a]thieno[2,3-d]pyrimidine-7-carbonitrile

From 4.0 g (0.0133 mol) of 2-butyl-4-oxo-4H-pyrido[1,2-a]thieno-[2,3-d]pyrimidine-7-carboxamide (Example 24), 100 ml of phosphorus oxychloride and 100 ml of chloroform and refluxing on a steam bath for four hours, following the procedure of Example 27, there is obtained 2.1 g of 2-butyl-4-oxo-4H-pyrido-[1,2-a]thieno[2,3-d]pyrimidine-7-carbonitrile; mp 216°–217° C. after recrystallization from pyridine.

EXAMPLE 31

4-Oxo-2-phenyl-4H-pyrido[1,2-a]thieno[2,3-d]pyrimidine-7-carbonitrile

From 3.2 g (0.01 mol) of 4-oxo-2-phenyl-4H-pyrido[1,2-a]thieno-[2,3-d]pyrimidine-7-carboxamide (Example 25), 90 ml of phosphorus oxychloride and 50 ml of chloroform and refluxing for twenty-four hours, following the procedure of Example 27, there is obtained 2.5 g of 4-oxo-2-phenyl-4H-pyrido[1,2-a]thieno[2,3-d]-pyrimidine-7-carbonitrile; mp 349°–351° C. after recrystallization from pyridine.

EXAMPLE 32

2,3-Dimethyl-4-oxo-4H-pyrido[1,2-a]thieno[2,3-d]pyrimidine-7-carbonitrile

From 1.0 g (0.0037 mol) of 2,3-dimethyl-4-oxo-4H-pyrido[1,2-a]-thieno[2,3-d]pyrimidine-7-carboxamide (Example 26), 50 ml of phosphorus oxychloride and 50 ml of chloroform and refluxing on a steam bath for eighteen hours, following the procedure of Example 27, there is obtained 0.89 g of 2,3-dimethyl-4-oxo-4H-pyrido[1,2-a]thieno[2,3-d]pyrimidine-7-carbonitrile; mp 306°–307° C. after recrystallization from glacial acetic acid.

EXAMPLE 33

2-Methyl-7-(1H-tetrazol-5-yl)-4H-pyrido[1,2-a]thieno[2,3-d]-pyrimidin-4-one

A mixture of 1.5 g (0.0062 mol) of 2-methyl-4-oxo-4H-pyrido-[1,2-a]thieno[2,3-d]pyrimidine-7-carbonitrile (Example 27), 1.36 g (0.021 mol) of sodium azide and 1.24 g (0.023 mol) of ammonium chloride in 280 ml of dimethylformamide is heated at 110°–120° C. for twelve hours. The reaction mixture is cooled, poured into 1 l of ice water and acidified with concentrated hydrochloric acid. The resulting precipitate is filtered and dissolved in hot glacial acetic acid, activated charcoal (Darco-G60, Matheson, Coleman and Bell) is added and the hot suspension is filtered through Supercell Hyflo ® (Johns-Manville). The filtrate is cooled to give 0.1 g of 2-methyl-7-(1H-tetrazol-5-yl)-4H-pyrido[1,2-a]thieno[2,3-d]pyrimidin-4-one; mp 330°–340° C. (dec) after recrystallization from pyridine.

EXAMPLE 34

2-Ethyl-7-(1H-tetrazol-5-yl)-4H-pyrido[1,2-a]thieno[2,3-d]-pyrimidin-4-one

A mixture of 0.65 g (0.0026 mol) of 2-ethyl-4-oxo-4H-pyrido-[1,2-a]thieno[2,3-d]pyrimidine-7-carbonitrile (Example 28), 0.56 g (0.0086 mol) of sodium azide and 0.51 g (0.0095 mol) of ammonium chloride in 80 ml of dimethylformamide is heated at 100° C. for twenty-four hours. The reaction mixture is cooled, poured into 900 ml of ice water and acidified with concentrated hydrochloric acid. The resulting precipitate of 2-ethyl-7-(1H-tetrazol-5-yl)-4H-pyrido[1,2-a]thieno[2,3-d]pyrimidin-4-one, 0.2 g, is collected; mp 293°–295° C. (dec) after recrystallization from pyridine.

EXAMPLE 35

2-Propyl-7-(1H-tetrazol-5-yl)-4H-pyrido[1,2-a]thieno[2,3-d]pyrimidin-4-one

From 0.85 g (0.0032 mol) of 4-oxo-2-propyl-4H-pyrido[1,2-a]thieno[2,3-d]pyrimidine-7-carbonitrile, (Example 29), 0.68 g (0.011 mol) of sodium azide and 0.62 g (0.012 mol) of ammonium chloride in 80 ml of dimethylformamide, following the procedure of Example 34, there is obtained 0.46 g of 2-propyl-7-(1H-tetrazol-5-yl)-4H-pyrido[1,2-a]thieno[2,3-d]pyrimidin-4-one; mp 288°–292° C. (dec) after recrystallization from pyridine.

EXAMPLE 36

2-Butyl-7-(1H-tetrazol-5-yl)-4H-pyrido[1,2-a]thieno[2,3-d]pyrimidin-4-one

From 7 g (0.025 mol) of 2-butyl-4-oxo-4H-pyrido[1,2-a]thieno-[2,3-d]pyrimidine-7-carbonitrile (Example 30), 8.45 g (0.13 mol) of sodium azide and 6.85 g (0.13 mol) of ammonium chloride in 250 ml of dimethylformamide heated at 125°–128° C. under a nitrogen atmosphere, following the procedure of Example 34, there is obtained 4.6 g of 2-butyl-7-(1H-tetrazol-5-yl)-4H-pyrido[1,2-a]thieno[2,3-d]pyrimidin-4-one; mp 281° C. (dec) after recrystallization from dimethylformamide-methanol.

EXAMPLE 37

2-Phenyl-7-(1H-tetrazol-5-yl)-4H-pyrido[1,2-a]thieno[2,3-d]pyrimidin-4-one

A mixture of 1.5 g (0.005 mol) of 4-oxo-2-phenyl-4H-pyrido-[1,2-a]thieno[2,3-d]pyrimidine-7-carbonitrile (Example 31), 1.0 g (0.0153 mol) of sodium azide and 0.9 g (0.0168 mol) of ammonium chloride in 200 ml of dimethylformamide is heated at 110°–120° C. for three days. The reaction mixture is cooled, poured into 1 l of ice water and acidified with concentrated hydrochloric acid. The resulting precipitate is filtered and dissolved in hot pyridine, activated charcoal (Darco-G60, Matheson, Coleman and Bell) is added and the hot suspension is filtered through Supercell Hyflo ® (Johns-Manville). The filtrate is cooled to give 0.55 g of 2-phenyl-7-(1H-tetrazol-5-yl)-4H-pyrido[1,2-a]thieno[2,3-d]pyrimidin-4-one; mp 310°–312° C. (dec) after recrystallization from pyridine.

EXAMPLE 38

2,3-Dimethyl-7-(1H-tetrazol-5-yl)-4H-pyrido[1,2-a]thieno[2,3-d]pyrimidin-4-one From 0.43 g (0.0017 mol) of 2,3-dimethyl-4-oxo-4H-pyrido[1,2-a]thieno[2,3-d]pyrimidine-7-carbonitrile (Example 32), 0.33 g (0.0051 mol) of sodium azide and 0.3 g (0.0056 mol) of ammonium chloride in 80 ml of dimethylformamide, following the procedure of Example 34, there is obtained 0.14 g of 2,3-dimethyl-7-(1H-tetrazol-5-yl)-4H-pyrido[1,2-a]thieno[2,3-d]pyrimidin-4-one with pyridine (1:0.6); mp 292°–294° C. (dec) after recrystallization from pyridine.

EXAMPLE 39

6-[(5-Butyl-3-carboxy-2-thienyl)amino]-3-pyridinecarboxylic acid

A mixture of 2-butyl-4-oxo-4H-pyrido[1,2-a]thieno[2,3-d]pyrimidine-7-carboxylic acid, methyl ester (Example 8), 0.94 g (0.00297 mol), 35 ml of 1 N sodium hydroxide and 25 ml of ethanol is refluxed for fifty-five minutes. The resulting solution is evaporated to dryness, and the residue is dissolved in hot water, filtered, cooled and acidified with glacial acetic acid. The precipitate is separated, washed with water and dried to give 0.7 g of 6-[(5-butyl-3-carboxy-2-thienyl)amino]-3-pyridinecarboxylic acid; mp 217° C. (dec) after recrystallization from glacial acetic acid.

EXAMPLE 40

2-Butyl-4-oxo-4H-pyrido[1,2-a]thieno[2,3-d]pyrimidine-7-carboxylic acid

A mixture of 6-[(5-butyl-3-carboxy-2-thienyl)amino]-3-pyridinecarboxylic acid (Example 39), 1.0 g (0.00312 mol), 25 ml of concentrated hydrochloric acid and 25 ml of water is refluxed in a wax bath under a nitrogen atmosphere at a bath temperature of 142° C. for seventeen and three-quarter hours. The suspension is cooled to room temperature and the precipitate is separated, washed with water and then washed with diethyl ether and dried to give 0.595 g of 2-butyl-4-oxo-4H-pyrido[1,2-a]thieno[2,3-d]pyrimidine-7-carboxylic acid; mp 252°–254° C. after recrystallization from ethanol.

EXAMPLE 41

2-Butyl-4-oxo-N-1H-tetrazol-5-yl-4H-pyrido[1,2-a]thieno[2,3-d]pyrimidine-7-carboxamide A mixture of 6-[(5-butyl-3-carboxy-2-thienyl)amino]-3-pyridinecarboxylic acid (Example 39), 3.2 g (0.01 mol) and 9.93 g (0.06 mol) of 1,1¹-carbonyldiimidazole (Aldrich Chemical Company) in 100 ml of dimethylformamide is heated in a wax bath under a nitrogen atmosphere with stirring at 100° to 108° C. for seventy minutes, cooled and stirred at room temperature for one hour. To the previous mixture is added 5-aminotetrazole monohydrate (Aldrich Chemical Company), 2.06 g (0.02 mol) and the mixture is heated at 100°–108° C. for ninety minutes. The solvent is evaporated and the residue dissolved in dimethylformamide, filtered, cooled and the precipitate collected and washed with methanol to give 1.2 g of 2-butyl-4-oxo-N-1H-tetrazol-5-yl-4H-pyrido[1,2-a]thieno[2,3-d]pyrimidine-7-carboxamide; mp 293° C. (dec) after recrystallization from pyridine.

EXAMPLE 42

2-Methyl-10-oxo-10H-pyrido[1,2-a]thieno[3,2-d]pyrimidine-7-carboxylic acid

A mixture of 1.7 g (0.01 mol) of 3-amino-5-methyl-2-thiophene-carboxylic acid, methyl ester (German Patent No. 1055007, Apr. 16, 1959) and 1.6 g (0.01 mol) of 6-chloro-3-pyridinecarboxylic acid (Aldrich Chemical Company) is heated in an oil bath at 180° C. for two hours. The mixture is cooled, dissolved in hot methanol, cooled and 0.23 g of 2-methyl-10-oxo-10H-pyrido[1,2-a]thieno[3,2-d]pyrimidine-7-carboxylic acid is collected; mp 338°–340° C. after recrystallization from methanol.

EXAMPLE 43

2-Methyl-10-oxo-10H-pyrido[1,2-a]thieno[3,2-d]pyrimidine-7-carboxylic acid, methyl ester A mixture of 5 g (0.0292 mol) of 3-amino-5-methyl-2-thiophene-carboxylic acid, methyl ester (German Patent No. 1055007, Apr. 16, 1959) and 5 g (0.0292 mol) of 6-chloro-3-pyridinecarboxylic acid, methyl ester (Alfred Bader Chemical Company) is heated in an oil bath at 180° C. for thirty minutes. The mixture is cooled, dissolved in hot methanol, cooled and 1.2 g of 2-methyl-10-oxo-10H-pyrido[1,2-a]thieno[3,2-d]pyrimidine-7-carboxylic acid, methyl ester is collected; mp 215°–216° C. after recrystallization from methanol.

EXAMPLE 44

2-Methyl-10-oxo-10H-pyrido[1,2-a]thieno[3,2-d]pyrimidine-7-carboxamide

A mixture of 2.7 g (0.0158 mol) of 3-amino-5-methyl-2-thiophene-carboxylic acid, methyl ester (German Patent No. 1055007, Apr. 16, 1959) and 2.5 g (0.0158 mol) of 6-chloro-3-pyridinecarboxamide (Aldrich Chemical Company) is heated in an oil bath at 180°–190° C. for one hour. The mixture is cooled and then suspended in hot chloroform and filtered to give 0.6 g of 2-methyl-10-oxo-10H-pyrido[1,2-a]thieno[3,2-d]pyrimidine-7-carboxamide; mp 375°–377° C. after recrystallization from pyridine.

EXAMPLE 45

2-Methyl-10-oxo-10H-pyrido[1,2-a]thieno[3,2-d]pyrimidine-7-carbonitrile

2-Methyl-10-oxo-10H-pyrido[1,2-a]thieno[3,2-d]pyrimidine-7-carboxamide (Example 44), 0.6 g (0.0023 mol), in 10 ml of pyridine, 25 ml of phosphorus oxychloride and 25 ml of chloroform is refluxed on a steam bath for three hours. The solvents are evaporated in vacuo and the residue is treated with 100 ml of ice water. The resulting precipitate is filtered to give 0.5 g of 2-methyl-10-oxo-10H-pyrido[1,2-a]thieno[3,2-d]pyrimidine-7-carbonitrile; mp 258°–259° C. after recrystallization from methanol.

EXAMPLE 46

2-Methyl-7-(1H-tetrazol-5-yl)-10H-pyrido[1,2-a]thieno[3,2-d]pyrimidin-10-one

A mixture of 0.21 g (0.00087 mol) of 2-methyl-10-oxo-10H-pyrido[1,2-a]thieno[3,2-d]pyrimidine-7-carbonitrile (Example 45), 0.2 g (0.0031 mol) of sodium azide and 0.166 g (0.0031 mol) of ammonium chloride in 50 ml of dimethylformamide is stirred and heated to 100° C. for twenty-four hours. The reaction mixture is cooled, poured into 900 ml of ice water and acidified with concentrated hydrochloric acid. The resulting precipitate is filtered to give 0.2 g of 2-methyl-7-(1H-tetrazol-5-yl)-10H-pyrido[1,2-a]thieno[3,2-d]pyrimidin-10-one; mp 321°–325° C. (dec) after recrystallization from pyridine.

EXAMPLE 47

2-Methyl-10-oxo-N-1H-tetrazol-5-yl-4H-pyrido[1,2-a]thieno[3,2-d]pyrimidine-7-carboxamide 0.33 g (0.0013 mol) of 2-methyl-10-oxo-10H-pyrido[1,2-a]thieno[3,2-d]pyrimidine-7-carboxylic acid (Example 42) and 0.29 g (0.0018 mol) of 1,1¹-carbonyldiimidazole (Aldrich Chemical Company) in 50 ml of dimethylformamide are stirred at 50° C. for one hour. To 0.15 g (0.00143 mol) of 5-aminotetrazole monohydrate (Aldrich Chemical Company) in 50 ml of dimethylformamide cooled to 0°–5° C. is added 0.7 ml (0.0054 mol) of chlorotrimethylsilane (Aldrich Chemical Company) and 0.75 ml (0.0054 mol) of triethylamine. After thirty minutes the mixture is allowed to reach room temperature and is stirred for an additional two hours. This mixture is combined with the previous cooled imidazolide mixture and stirred for fourteen hours at room temperature. The resulting precipitate is collected, slurried in boiling glacial acetic acid, the mixture is cooled and filtered to give 0.15 g of 2-methyl-10-oxo-N-1H-tetrazol-5-yl-4H-pyrido[1,2-a]thieno[3,2-d]pyrimidine-7-carboxamide; mp 342°–344° C. (dec) after recrystallization from pyridine.

EXAMPLE 48

1,3-Dimethyl-10-oxo-10H-pyrido[1,2-a]thieno[3,4-d]pyrimidine-7-carboxylic acid

A mixture of 18.5 g (0.1 mol) of 4-amino-2,5-dimethyl-3-thiophene-carboxylic acid, methyl ester and 15.76 g (0.1 mol) of 6-chloro-3-pyridinecarboxylic acid (Aldrich Chemical Company) is heated in a wax bath at 168°–186° C. for one hundred ten minutes and then at 185°–186° C. for ninety minutes under nitrogen. The mixture is cooled, suspended in hot methanol, cooled and 4.2 g of crude product is collected. This material is dissolved in hot pyridine, activated charcoal (Darco- G60, Matheson, Coleman and Bell) is added and the hot suspension is filtered through Supercell Hyflo ® (Johns-Manville). The filtrate is cooled to give 1.75 g of 1,3-dimethyl-10-oxo-10H-pyrido[1,2-a]thieno[3,4-d]pyrimidine-7-carboxylic acid; mp 336° C. (dec) after recrystallization from pyridine.

EXAMPLE 49

1,3-Dimethyl-10-oxo-10H-pyrido[1,2-a]thieno[3,4-d]pyrimidine-7-carboxylic acid, methyl ester A mixture of 2.5 g (0.0113 mol) of 4-amino-2,5-dimethyl-3-thiophenecarboxylic acid, methyl ester and 2.5 g (0.0113 mol) of 6-chloro-3-pyridinecarboxylic acid, methyl ester (Alfred Bader Chemical Company) is heated in an oil bath at 180° C. for thirty minutes. The mixture is cooled, dissolved in hot methanol, cooled and 0.3 g of 1,3-dimethyl-10-oxo-10H-pyrido[1,2-a]thieno[3,4-d]pyrimidine-7-carboxylic acid, methyl ester is collected; mp 209°–210° C. after recrystallization from methanol.

EXAMPLE 50

1,3-Dimethyl-10-oxo-10H-pyrido[1,2-a]thieno[3,4-d]pyrimidine-7-carboxamide

A mixture of 5 g (0.0226 mol) of 4-amino-2,5-dimethyl-3-thiophene-carboxylic acid, methyl ester and 3.5 g (0.0226 mol) of 6-chloro-3-pyridinecarboxamide (Aldrich Chemical Company) is heated in an oil bath at 180° C. for thirty minutes. The mixture is cooled, dissolved in hot pyridine, cooled, the precipitate collected and dissolved in hot methanol, activated charcoal (Darco-G60, Matheson, Coleman and Bell) is added and the hot suspension is filtered through Supercell Hyflo ® (Johns-Manville). The filtrate is cooled to give 0.2 g of 1,3-dimethyl-10-oxo-10H-pyrido[1,2-a]thieno[3,4-d]pyrimidine-7-carboxamide with methanol (1:0.125); mp 272°–275° C. after recrystallization from methanol.

EXAMPLE 51

1,3-Dimethyl-10-oxo-10H-pyrido[1,2-a]thieno[3,4-d]pyrimidine-7-carbonitrile 1,3-Dimethyl-10-oxo-10H-pyrido[1,2-a]thieno[3,4-d]pyrimidine-7-carboxamide (Example 50), 0.6 g (0.0022 mol), in 10 ml of pyridine, 25 ml of phosphorus oxychloride and 25 ml of chloroform is refluxed on a steam bath for two hours. The solvents are evaporated in vacuo and the residue is treated with 100 ml of water. The resulting precipitate is filtered to give 0.3 g of 1,3-dimethyl-10-oxo-10H-pyrido[1,2-a]thieno[3,4-d]pyrimidine-7-carbonitrile with methanol (1:0.125); mp 242°–244° C. after recrystallization from methanol.

EXAMPLE 52

1,3-Dimethyl-7-(1H-tetrazol-5-yl)-10H-pyrido[1,2-a]thieno[3,4-d]-pyrimidin-10-one A mixture of 4.4 g (0.0172 mol) of 1,3-dimethyl-10-oxo-10H-pyrido-[1,2-a]thieno[3,4-d]pyrimidine-7-carbonitrile (Example 51), 6.5 g (0.1 mol) of sodium azide and 5.3 g (0.1 mol) of ammonium chloride in 180 ml of dimethylformamide is stirred and heated in a wax bath at 120° C. for seventeen hours under nitrogen. The reaction mixture is cooled, filtered and the filtrate evaporated. The residue is treated with 250 ml of water and acidified with concentrated hydrochloric acid. This mixture is warmed on a steam bath, cooled and filtered to give 5.1 g of crude product. This material is dissolved in hot pyridine, activated charcoal (Darco-G60, Matheson, Coleman and Bell) is added and the hot suspension is filtered through Supercell Hyflo ® (Johns-Mansville). The filtrate is cooled to give 3.1 g of 1,3-dimethyl-7-(1H-tetrazol-5-yl)-10H-pyrido[1,2-a]thieno-[3,4-d]pyrimidin-10-one; mp 292° C. (dec).

EXAMPLE 53

1,3-Dimethyl-10-oxo-N-1H-tetrazol-5-yl-10H-pyrido[1,2-a]thieno-[3,4-d]pyrimidine-7-carboxamide A mixture of 0.6 g (0.0022 mol) of 1,3-dimethyl-10-oxo-10H-pyrido-[1,2-a]thieno[3,4-d]pyrimidine-7-carboxylic acid (Example 48) and 0.84 g (0.005 mol) of 1,1′ carbonyldiimidazole (Aldrich Chemical Company) in 90 ml of dimethylformamide is stirred and heated in a wax bath at 105° C. for eighty five minutes under nitrogen. The mixture is allowed to stand at room temperature for thiry minutes and then 0.225 g (0.0022 mol) of 5-aminotetrazole monohydrate (Aldrich Chemical Company) is added and the mixture heated at 105° C. for three and one-half hours. The solvent is evaporated and the residue suspended in hot methanol, cooled and 0.71 g of crude product is collected. This material is dissolved in hot pyridine, activated charcoal (Darco G60, Matheson, Coleman and Bell) is added and the hot suspension is filtered through Supercell Hyflo ® (Johns-Manville). The filtrate is cooled to give 0.47 g of 1,3-dimethyl-10-oxo-N-1H-tetrazol-5-yl-10H-pyrido-[1,2-a]thieno[3,4-d]pyrimidine-7-carboxamide with pyridine (1:0.2); mp >300° C. (dec).

EXAMPLE 54

Ethyl 10-oxo-10H-pyrido[1,2-a]thieno[3,4-d]pyrimidine-7-carboxylate

A mixture of ethyl 3,10-dihydro-10-oxo-1H-pyrido[1,2-a]thieno-[3,4-d]pyrimidine-7-carboxylate (2.0 g., 0.0072 mol) and m-chloroperbenzoic acid (1.47 g., 0.0072 mol) in chloroform (75 ml) is stirred at room temperature overnight. The solvent is evaporated at reduced pressure to give a syrup, which crystallizes from ethanol. Recrystallization from ethanol, silica gel chromatography and a further recrystallization from ethanol gives the product as yellow crystals (mp 175° C.).

EXAMPLE 55

Ethyl 10-oxo-10H-pyrido[1,2-a]thieno[3,4-d]pyrimidine-7-carboxylate

A mixture of ethyl 3,10-dihydro-10-oxo-1H-pyrido[1,2-a]thieno-[3,4-d]pyrimidine-7-carboxylate (2.0 g., 0.0072 mol) and N-chlorosuccinimide (0.97 g., 0.0072 mol) in pyridine (20 ml) is heated on a steam bath for 18 minutes. The reaction mixture is cooled and poured into a large volume of ice water. The precipitate is filtered, washed with water and dried. Recrystallization from ethanol gives the product (1.1 g.), mp 175°–176° C.

EXAMPLE 56

3-Chloro-10-oxo-10H-pyrido-[1,2-a]thieno[3,4-d]pyrimidine-7-carboxylic acid

Chlorotrimethylsilane (0.4 ml, 0.03 mol) is added to a cooled (ice bath) solution of 3,10-dihydro-10-oxo-1H-pyrido[1,2-a]thieno-[3,4-d]pyrimidine-7-carboxylic acid (0.75 g., 0.03 mol) in pyridine (5 ml) under nitrogen. The mixture is stirred at ice bath temperatures for one hour and then allowed to warm to room temperature. N-Chlorosuccinimide (0.8 g., 0.06 mol) is addd and the mixture is heated at 95° C. for 20 minutes. The mixture is cooled, diluted with water (3 ml) and stirred for 15 minutes. The precipitate is filtered off, dried and recrystallized from ethanol to give the product (0.5 g.), mp 285° C. (dec).

EXAMPLE 57

10-oxo-10H-pyrido[1,2-a]thieno[3,4-d]pyrimidine-7-carboxylic acid

Chlorotrimethylsilane (2.6 ml, 0.02 mol) is added to a cooled (icebath) solution of 3,10-dihydro-10-oxo-1H-pyrido[1,2-a]thieno-[3,4-d]pyrimidine-7-carboxylic acid (5.0 g., 0.02 mol) in pyridine (40 ml) under nitrogen. The mixture is stirred at ice bath temperature for one hour and then allowed to warm to room temperature. N-Chlorosuccinimide (2.74 g., 0.02 mol) is added and the mixture is heated at 90°–95° C. for 20 minutes. The mixture is cooled, diluted with water (5 ml) and stirred for 15 minutes. The precipitate is filtered off, dried, washed with boiling acetone (3×100 ml) and recrystallized from dimethylformamide to give the product (3.9 g.), mp 320° C. (dec).

EXAMPLE 58

10-oxo-N-1H-tetrazol-5-yl-10H-pyrido[1,2-a]thieno[3,4-d]-pyrimidine-7-carboxamide A mixture of 10-oxo-10H-pyrido[1,2-a]thieno[3,4-d]pyrimidine-7-carboxylic acid (0.7 g., 0.003 mol) and 1,1'-carbonyldiimidazole (0.94 g., 0.006 mol) in dimethylformamide (25 ml) is heated at 100° C. with stirring under nitrogen for 1.5 hours. 5-Aminotetrazole monohydrate (0.3 g., 0.003 mol) is added and the resulting mixture is heated at 100° C. for 2 hours. The reaction mixture is cooled and diluted with acetone. The precipitate is filtered off, washed with boiling dimethylformamide, and dried to give the product (0.46 g.), mp 280° C. (dec).

EXAMPLE 59

10-oxo-10H-pyrido[1,2-a]thieno[3,4-d]pyrimidine-7-carboxamide

A mixture of 10-oxo-10H-pyrido[1,2-a]thieno[3,4-d]pyrimidine-7-carboxylic acid (6.0 g., 0.024 mol) and 1,1'-carbonyldiimidazole (4.0 g., 0.024 mol) in dimethylformamide (120 ml) is heated at 110° C. for 2.5 hours under nitrogen. The solution is cooled in an ice bath and anhydrous ammonia is bubbled through for 15 minutes. The mixture is stirred at ice bath temperature for 2 hours and at room temperature for one hour. The precipitate is filtered off, washed with tetrahydrofuran and dried to give the product (5.2 g.), mp 340° C. (dec).

EXAMPLE 60

10-oxo-10H-pyrido[1,2-a]thieno[3,4-d]pyrimidine-7-carbonitrile

A mixture of 10-oxo-10H-pyrido[1,2-a]thieno[3,4-d]pyrimidine-7-carboxamide (3.8 g., 0.015 mol), p-toluenesulfonyl chloride (4.4 g., 0.023 mol) and pyridine (3.8 ml, 0.046 mol) in dimethylformamide (50 ml) is heated at 95° C. for 1 hour. The mixture is cooled, diluted with water (5 ml) and stirred. The precipitate is filtered, washed with water and dried. Recrystallization from 2-propanol gives golden crystals (2.5 g.) mp 233°–234° C.

EXAMPLE 61

Ethyl 10-oxo-10H-pyrido[1,2-a]thieno[3,2-d]pyrimidine-7-carboxylate

A mixture of ethyl 3,10-dihydro-10-oxo-1H-pyrido[1,2-a]thieno-[3,2-d]pyrimidine-7-carboxylate (0.4 g., 0.0014 mol) and N-chlorosuccinimide (0.9 g., 0.0014 mol) in pyridine (4 ml) is heated on a steam bath for 18 minutes. The reaction mixture is cooled and poured into a large volume of ice water. The precipitate is filtered, washed with water and dried. Recrystallization from ethanol gives the product (0.2 g.) mp 188°–190° C.

EXAMPLE 62

10-Oxo-10H-pyrido[1,2-a]thieno[3,2-d]pyrimidine-7-carboxylic acid

Chlorotrimethylsilane (2.35 ml, 0.018 mol) is added to a cooled (ice bath) solution of 3,10-dihydro-10-oxo-1H-pyrido[1,2-a]-thieno[3,2-d]pyrimidine-7-carboxylic acid (4.5 g, 0.018 mol) in pyridine (35 ml) under nitrogen. The mixture is stirred at ice bath temperature for 1 hour and then allowed to warm at room temperature. N-chlorosuccinimide (2.44 g, 0.018 mol) is added and the mixture is heated at 95° C. for 20 minutes. The mixture is cooled, diluted with ice water (5 ml) and stirred for 15 minutes. The precipitate is filtered, washed with boiling acetone and dried to give the product (3.5 g.) mp 335° C. (dec).

EXAMPLE 63

10-oxo-N-1H-tetrazol-5-yl-10H-pyrido[1,2-a]thieno[3,2-d]-pyrimidine-7-carboxamide A mixture of 10-oxo-10H-pyrido[1,2-a]thieno[3,2-d]pyrimidine-7-carboxylic acid (1.0 g, 0.0041 mol) and 1,1'-carbonyldiimidazole (1.35 g, 0.0082 mol) in dimethylformamide (10 ml) is heated at 95°–100° C. with stirring under nitrogen for 1.5 hours. 5-Aminotetrazole monohydrate (0.42 g, 0.0041 mol) is added and the resulting mixture is heated at 100° C. for 1–5 hours. The precipitate is filtered off, washed with tetrahydrofuran and recrystallized from dimethylformamide to give the product (0.6 g.), mp 295°–296° C.

EXAMPLE 64

10-Oxo-10H-pyrido[1,2-a]thieno[3,2-d]pyrimidine-7-carboxamide

A mixture of 10-oxo-10H-pyrido[1,2-a]thieno[3,2-d]pyrimidine-7-carboxylic acid (2.5 g, 0.01 mol) and 1,1'-carbonyldiimidazole (1.7 g, 0.01 mol) in dimethylformamide (25 ml) is heated at 90°–95° C. for one hour under nitrogen. The solution is cooled in an ice bath and anhydrous ammonia is bubbled through for 15 minutes. The mixture is stirred at ice bath temperature for 2 hours and at room temperature for one hour. The reaction mixture is cooled and the precipitate is filtered off. The precipitate is washed with tetrahydrofuran and recrystallized from dimethylformamide to give the product (1.2 g.), mp 319°–320° C.

EXAMPLE 65

10-Oxo-10H-pyrido[1,2-a]thieno[3,2-d]pyrimidine-7-carbonitrile

A mixture of 10-oxo-10H-pyrido[1,2-a]thieno[3,2-d]pyrimidine-7-carboxamide (1.4 g, 0.006 mol), p-toluenesulfonyl chloride (1.6 g, 0.008 mol), and pyridine (1.4 ml, 0.017 mol) in dimethylformamide (10 ml) is heated at 95° C. for 75 minutes. The mixture is cooled, diluted with water (5 ml) and stirred. The precipitate is filtered, washed with water, with ethanol and dried. Recrystallization from dimethylformamide gives the product (0.8 g.), mp 263°–264° C. (dec).

EXAMPLE 66

7-(1H-Tetrazol-5-yl)-10H-pyrido[1,2-a]thieno[3,2-d]pyrimidin-10-one

A mixture of 10-oxo-10H-pyrido[1,2-a]thieno[3,2-d]pyrimidine-7-carbonitrile (0.6 g., 0.0026 mol), sodium azide (0.56 g., 0.0086 mol) and ammonium chloride (0.46 g., 0.0036 mol) in dimethylformamide (75 ml) is heated at 100°–105° C. for 18 hours under nitrogen. The reaction mixture is cooled, poured into ice water (700 ml) and acidified with concentrated hydrochloric acid (1 ml). The precipitate is filtered off, washed with water, with acetone and dried. Recrystallization from dimethylformamide gives a crystalline product (0.39 g.) mp 300° C. (dec).

EXAMPLE 67

10-Oxo-10H-pyrido[1,2-a]thieno[3,4-d]pyrimidine-7-carbonitrile hydrochloride salt A mixture of 10-oxo-10H-pyrido[1,2-a]thieno[3,4-d]pyrimidine-7-carboxamide (0.3 g., 0.0012 mol) and thionyl chloride (0.18 ml, 0.0025 mol) in dimethylformamide (5 ml) is heated at 70° C. under nitrogen for 4 hours. The reaction mixture is cooled in an ice bath. The product, which precipitates, is filtered off and washed with water. Recrystallization from dimethylformamide gives a crystalline product (0.15 g.), mp 294° C. (dec).

EXAMPLE 68

7-(1H-Tetrazol-5-yl)-10H-pyrido[1,2-a]thieno[3,4-d]pyrimidine-10-one

A mixture of 10-oxo-10H-pyrido[1,2-a]thieno[3,4-d]pyrimidine-7-carbonitrile (0.058 g., 0.0003 mol), sodium azide (0.074 g., 0.0011 mol) and ammonium chloride (0.061 g., 0.0011 mol) in dimethylformamide (15 ml) is heated at 95°–100° C. under nitrogen for 46 hours. The solvent is evaporated. The residue is triturated with 1 N hydrochloric acid, filtered and sucked dry to give the product, mp 300° C. (dec).

EXAMPLE 69

3-Methyl-4-oxo-4H-pyrido[1,2-a]thieno[2,3-d]pyrimidine-7-carboxylic acid, methyl ester A mixture of 11.27 g (0.066 mol) of 2-amino-4-methyl-3-thiophenecarboxylic acid, methyl ester (*Chemische Berichte*, Vol. 98, pages 3571–3577, 1965) and 11.3 g (0.066 mol) of 6-chloro-3-pyridinecarboxylic acid, methyl ester (Alfred Bader Chemical Company) is heated in a wax bath at 173°–190° C. for 220 minutes under nitrogen. The distillate is collected in a Dean-Stark trap attached to the reaction flask. The mixture is cooled, dissolved in hot methanol, cooled and 0.61 g of 3-methyl-4-oxo-4H-pyrido[1,2-a]thieno[2,3-d]pyrimidine-7-carboxylic acid, methyl ester is collected; mp 208°–209° C. after recrystallization from dichloromethane-methanol.

EXAMPLE 70

2-Ethyl-4-oxo-4H-pyrido[1,2-a]thieno[2,3-d]pyrimidine-7-carboxylic acid, monohydrochloride To a cooled solution of 2-ethyl-4-oxo-4H-pyrido[1,2-a]thieno[2,3-d]pyrimidine-7-carboxylic acid (Example 2), 0.2 g (0.00073 mol), in 50 ml of 2-propanol, is added a slight excess of a solution of dry hydrogen chloride in 2-propanol. After 10 minutes, 500 ml of anhydrous ether is added to the previous solution and the precipitate filtered to give 0.1 g of 2-ethyl-4-oxo-4H-pyrido[1,2-a]thieno[2,3-d]pyrimidine-7-carboxylic acid, monohydrochloride; mp 255°–256° C. after recrystallization from 2-propanol-ether.

EXAMPLE 71

2-Ethyl-4-oxo-4H-pyrido[1,2-a]thieno[2,3-d]pyrimidine-7-carboxylic acid, monosodium salt, monohydrate To a cooled solution of 2-ethyl-4-oxo-4H-pyrido[1,2-a]thieno[2,3-d]pyrimidine-7-carboxylic acid (Example 2), 0.3 g (0.0011 mol) in 20 ml of dimethylacetamide, is added 0.35 ml (0.0011 mol) of a 3.2 molar solution of sodium 2-ethylhexanoate in dimethylacetamide. After 15 minutes, 500 ml of ethyl acetate is added to the previous solution and the precipitate filtered to give 0.15 g of 2-ethyl-4-oxo-4H-pyrido[1,2-a]thieno[2,3-d]pyrimidine-7-carboxylic acid, monosodium salt, monohydrate; mp 388°–390° C.

STARTING MATERIALS

The starting materials employed in the foregoing examples are obtained by the methods described in the following:

A. 2-Amino-5-butyl-3-thiophenecarboxylic acid, methyl ester

Triethylamine, 150 ml (1.08 mol), is added to a stirred suspension of methyl cyanoacetate, 198.18 g (2 mol) and sulfur, 64.12 g (2 mol), in 250 ml of dimethylformamide under a nitrogen atmosphere. Hexanal, 200.3 g (2 mol), is added dropwise with stirring to this mixture over fifty minutes while the temperature is maintained at ~50° C. The solution was allowed to reach room temperature and then stirred for twenty one hours, poured into 3 L of water and the aqueous layer extracted with 2 L of ether (2 times). The ether layer is separated and washed successively with 2 L of water (2 times), 2 L saturated NaCl solution (2 times), dried over anhydrous $Na_2SO_4$ and evaporated to give 187 g of 2-amino-5-butyl-3-thiophenecarboxylic acid, methyl ester; mp. 62°–63° C. after recrystallization from hexane.

B. 2-Amino-5-propyl-3-thiophenecarboxylic acid, ethyl ester

From 56.5 g (0.5 mol) of ethyl cyanoacetate, 16 g (0.5 mol) of sulfur, 50 ml (0.36 mol) of triethylamine, 43 g (0.5 mol) of pentanal and 200 ml of dimethylformamide, following the previous procedure (A) is obtained 52 g of 2-amino-5-propyl-3-thiophenecarboxylic acid, ethyl ester; bp 125°–135° C. at 200μ.

C. Tetrahydro-2,5-dimethyl-4-oxo-3-thiophenecarboxylic acid, methyl ester

A mixture of 83 g (0.83 mol) of methyl crotonate (Aldrich Chemical Company) and 100 g (0.83 mol) of methyl thiolactate (*Helvetica Chimica Acta*, Vol. 45, pages 1750–1765, 1962) in 800 ml of toluene is added dropwise to a stirred suspension of 64.8 g (1.2 mol) of sodium methoxide (Aldrich Chemical Company) in 500 ml of toluene. The suspension is stirred and refluxed for four and one-half hours, cooled, 500 ml of water is added and the mixture is made acidic by the addition of glacial acetic acid. The aqueous solution is extracted with toluene. The toluene layer is separated, washed successively with 200 ml of water, 200 ml of saturated sodium bicarbonate solution and 200 ml of water, dried over anhydrous $Na_2SO_4$, and the solution evaporated to give 90 g of tetrahydro-2,5-dimethyl-4-oxo-3-thiophenecarboxylic acid, methyl ester; bp 78°–80° C./0.04 mm.

D. Tetrahydro-4-(hydroxyimino)-2,5-dimethyl-3-thiophenecarboxylic acid, methyl ester Hydroxylamine hydrochloride, 145 g (2.09 mol), and barium carbonate (J. T. Baker Chemical Company), 219.2 g (1.11 mol), are added to a solution of 89.3 g (0.474 mol) of tetrahydro-2,5-dimethyl-4-oxo-3-thiophenecarboxylic acid, methyl ester (Example C) in 1 L of absolute ethanol. The suspension is stirred and refluxed for sixteen hours, cooled, filtered through Supercell Hyflo ® (Johns-Manville), the filtrate evaporated and the residue dissolved in 500 ml of diethyl ether. The diethyl ether solution is washed with 500 ml of water (2 times). The diethyl ether layer is separated, dried over anhydrous $Na_2SO_4$ and evaporated to give 83.7 g of tetrahydro-4-(hydroxyimino)-2,5-dimethyl-3-thiophene-carboxylic acid, methyl ester as an orange liquid.

E. 4-Amino-2,5-dimethyl-3-thiophenecarboxylic acid, methyl ester

A cooled solution of 80 g (0.39 mol) of tetrahydro-4-(hydroxyimino)-2,5-dimethyl-3-thiophenecarboxylic acid, methyl ester (Example D) in 1 L of anhydrous diethyl ether is saturated with dry hydrogen chloride over a period of one hour. The solution is stirred and allowed to reach room temperature over fourteen hours. The resulting precipitate is filtered, dissolved in 200 ml of water, neutralized with concentrated ammonium hydroxide and the aqueous solution is extracted with 200 ml of diethyl ether. The diethyl ether solution is washed with 100 ml of water. The diethyl ether layer is separated, dried over anhydrous $Na_2SO_4$ and evaporated to give 34 g of 4-amino-2,5-dimethyl-3-thiophenecarboxylic acid, methyl ester; mp 75°–77° C. after recrystallization from hexane.

F. 3,10-Dihydro-10-oxo-1H-pyrido[1,2-a]thieno[3,4-d]pyrimidine-7-carboxylic acid 6-Aminonicotinic acid (10 g., 0.072 mol) [Berichte, 26, 2187,(1893)], methyl 4-oxotetrahydro-thiophene-3-carboxylate (28 g., 0.175 mol) [Monats, Chem., 104, 1520(1973)] and p-toluenesulfonic acid monohydrate (1.0 g) are thoroughly mixed and heated at 170° C. under nitrogen for 75 minutes. The distillate is collected in a Dean-Stark trap. The residue is cooled, tritrated with boiling chloroform and filtered to give the product as a yellow powder (11.3 g.). Recrystallization from dimethylformamide gives an analytical sample mp 314°–315° C. (dec).

G. Ethyl 3,10-dihydro-10-oxo-1H-pyrido[1,2-a]thieno[3,4-d]pyrimidine-7-carboxylate Ethyl 6-aminonicotinate (2.5 g., 0.015 mol), methyl 4-oxotetrahydrothiophene-3-carboxylate (6.2 g., 0.039 mol) and p-toluenesulfonic acid monohydrate (0.25 g) are thoroughly mixed and heated at 155°–160° C. under nitrogen for 90 minutes. The distillate is collected in a Dean-Stark trap. The residue is cooled, triturated with boiling ethanol and filtered. Recrystallization from methanol gives yellow crystals (1.2 g.), mp 183°–185° C.

H. 3,10-Dihydro-10-oxo-1H-pyrido[1,2-a]thieno[3,4-d]pyrimidine-7-carboxylic acid A suspension of ethyl 3,10-dihydro-10-oxo-1H-pyrido[1,2-a]thieno[3,4d]pyrimidine-7-carboxylate (0.25 g., 0.001 mol) in 2 N hydrochloric acid is refluxed for 2.5 hours. The reaction mixture is cooled in an ice-bath. The product is filtered off and recrystallized from dimethylformamide to give yellow crystals (0.14 g.), mp 311°–312° C.

I. Ethyl 3,10-dihydro-10-oxo-1H-pyrido[1,2-a]thieno[3,4-d]pyrimidine-7-carboxylate A mixture of 3,10-dihydro-10-oxo-1H-pyrido[1,2-a]thieno-[3,4-d]pyrimidine-7-carboxylic Acid (15 g., 0.06 mol) and 1,1' carbonyldiimidazole (9.8 g, 0.06 mol) in dimethylformamide (12 ml) and tetrahydrofuran (700 ml) is refluxed with stirring for 3 hours. Absolute ethanol (20 ml) is added and refluxing is continued for a further 3 hours. The solvents are removed under reduced pressure. The residue is shaken with hot 0.5 mol aqueous sodium bicarbonate (200 ml), cooled and filtered. The residue is washed several times with water and recrystallized from methanol to give the product (8.9 g.) mp 183°–185° C.

J. 3,10-Dihydro-10-oxo-N-1H-tetrazol-5-yl-1H-pyrido[1,2-a]thieno[3,4-d]pyrimidine-7-carboxamide A mixture of 3,10-dihydro-10-oxo-N-1H-pyrido[1,2-a]thieno[3,4-d]pyrimidine-7-carboxylic acid (1.0 g., 0.004 mol) and 1,1'-carbonyldiimidazole (1.3 g., 0.008 mol) in tetrahydrofuran (75 ml) and dimethylformamide (2 ml) is refluxed with stirring under nitrogen for 1.5 hours. 5-Aminotetrazole monohydrate (0.4 g., 0.004 mol) is added and the resulting mixture is refluxed for 3 hous. The reaction mixture is cooled in an ice bath and the product is filtered off. Recrystallization from dimethylformamide gives the product (0.94 g.), mp 290° L C. (dec).

K. 3,10-Dihydro-10-oxo-1H-pyrido[1,2-a]thieno[3,4-d]pyrimidine-7-carboxamide A mixture of 3,10-dihydro-10-oxo-1H-pyridol[1,2-a]thieno[3,4-d]pyrimidine-7-carboxylic acid (4.4 g., 0.018 mol) and 1,1'-carbonyldiimidazole (2.9 g., 0.018 mol) in tetrahydrofuran (300 ml) and dimethylformamide (4 ml) is refluxed under nitrogen for 3.5 hours. The solution is cooled in an ice bath and anhydrous ammonia is bubbled through for 45 minutes. The precipitate is filtered off, washed with hot 0.5 M. aqueous sodium bicarbonate solution, with hot dimethylformamide with ether and dried to give a yellow powder (2.9 g.). mp 285° C. (dec).

L.
3,10-Dihydro-10-oxo-1H-pyrido[1,2-a]thieno[3,4-d]pyrimidine-7-carbonitrile A mixture of 3,10-dihydro-10-oxo-1H-pyrido[1,2-a]thieno[3,4-d]pyrimidine-7-carboxamide (2.9 g., 0.012 mol) and thionyl chloride (1.5 ml) in dimethylformamide (30 ml) is heated at 70° C. for 4 hours. The reaction mixture is cooled in an ice bath. The product, which precipitates, is filtered off and washed with water. Recrystallization from methanol gives a crystalline product (1.6 g.), mp 256°-257° C.

M.
3,10-Dihydro-10-oxo-7-(1H-tetrazol-5-yl)-1H-pyrido[1,2-a]thieno[3,4-d]pyrimidine A mixture of 3,10-dihydro-10-oxo-1H-pyrido[1,2-a]thieno[3,4-d]pyrimidine-7-carbonitrile (1.0 g., 0.004 mol), sodium azide (0.81 g., 0.012 mol) and ammonium chloride (0.69 g., 0.013 mol) in dimethylformamide (150 ml) is heated at 100°-105° C. for 18 hours. The solvent is removed at reduced pressure. The residue is triturated with 1 N hydrochloric acid, filtered, washed with water, dissolved in 10% aqueous potassium carbonate, filtered and reprecipitated with 1 N hydrochloric acid. The solid is filtered off and recrystallized from dimethylformamide-methanol to give a crystalline product (0.96 g.), mp 285° C.

N.
3,10-Dihydro-10-oxo-1H-pyrido[1,2-a]thieno[3,2-d]pyrimidine-7-carboxylic acid (I) and
3,10-dihydro-10-oxo-1H-pyrido-[1,2-a]thieno[3,4-d]pyrimidine-7-carboxylic acid (II)

6-Aminonicotinic acid (7.3 g, 0.053 mol), methyl 3-oxotetrahydrothiophene-2-carboxylate (containing methyl-4-oxotetrahydrothiophene-3-carboxylate) (27.6 g., 0.140 mol) and p-toluenesulfonic acid monohydrate (0.7 g) are thoroughly mixed and heated at 170° C. uner nitrogen for 75 minutes. The distillate is collected in a Dean-Stark trap. The residue is cooled, triturated with boiling chloroform and filtered to give a mixture of I and II as a yellow powder (10.4 g.), mp 300° C. (dec).

O. Ethyl
3,10-dihydro-10-oxo-1H-pyrido[1,2-a]thieno[3,2-d]pyrimidine-7-carboxylate(I) and ethyl
3,10-dihydro-10-oxo-1H-pyrido[1,2-a]thieno[3,4-d]pyrimidine-7-carboxylate(II)

A mixture of 3,10-dihydro-10-oxo-1H-pyrido[1,2-a]thieno[3,2-d]pyrimidine-7-carboxylic acid (containing 3,10-dihydro-10-oxo-1H-pyrido[1,2-a]thieno[3,4-d]pyrimidine-7-carboxylic acid) (10.4 g, 0.042 mol) and 1,1' carbonyldiimidazole (6.9 g, 0.042 mol) in dimethylformamide (10 ml) and tetrahydrofuran (500 ml) is refluxed with stirring for 3 hours. Absolute ethanol (20 ml) is added and refluxing is continued for a further 3 hours. The solvents are removed under reduced pressure to give a solid product. Recrystallization from 2-propanol gives a mixture of I and II (8.0 g.) mp 147°-149° C.

The mixture is dissolved in a minimum amount of chloroform and fractionated with a Waters preparative High Pressure Liquid Chromatography column (silica gel) using ethyl acetate as solvent. I is recrystallized from isopropyl ether-2-propranol to give yellow crystals (5.3 g.) mp 155°-156° C.

II is recrystallized from methanol to give a crystalline product (0.5 g.).

P.
3,10-Dihydro-10-oxo-1H-pyrido[1,2-a]thieno[3,2-d]pyrimidine-7-carboxylic acid A suspension of ethyl 3,10-dihydro-10-oxo-1H-pyrido[1,2-a]thieno[3,2-d]pyrimidine-7-carboxylate (5.0 g, 0.018 mol) in 2 N hydrochloric acid (60 ml) is refluxed for 3 hours. The reaction mixture is cooled in an ice-bath. The precipitate is filtered, washed with water, with acetone and dried to give the product (3.5 g.), mp 325° C. (dec).

Q.
3,10-Dihydro-10-oxo-1H-pyrido[1,2-a]thieno[3,2-d]pyrimidine-7-carboxamide A mixture of 3,10-dihydro-10-oxo-1H-pyrido[1,2-a]thieno[3,2-d]pyrimidine-7-carboxylic acid (3.0 g., 0.012 mol) and 1,1'-carbonyldiimidazole (2.0 g., 0.012 mol) in tetrahydrofuran (180 ml) and dimethylformamide (3.5 ml) is refluxed under nitrogen for 5 hours. The solution is cooled in an ice-bath and anhydrous ammonia is bubbled through for 15 minutes. The mixture is stirred at ice-bath temperature for 2 hours and at room temperature for one hour. The reaction mixture is cooled and the precipitate is filtered off and washed with tetrahydrofuran. The precipitate is treated with hot 0.5 mol aqueous sodium bicarbonate solution, filtered, washed with water, washed with acetone and sucked dry to give the product (2.0 g.), mp 334° C. (dec).

R.
3,10-Dihydro-10-oxo-1H-pyrido[1,2-a]thieno[3,2-d]pyrimidine-7-carbonitrile A mixture of 3,10-dihydro-10-oxo-1H-pyrido[1,2-a]thieno[3,2-d]pyrimidine-7-carboxamide (1.7 g., 0.007 mol), p-toluene-sulfonyl chloride (2.0 g., 0.01 mol) and pyridine (1.7 ml, 0.021 mol) in dimethylformamide (30 ml) is heated at 100° C. under nitrogen for 40 minutes. The reaction mixture is cooled and diluted with water (15 ml). The resulting aqueous solution is stirred for one hour. The precipitate is filtered off, washed with water and sucked dry. Recrystallization from methanol gives the product (1.1 g.), mp 261°-263° C.

S.
3,10-Dihydro-10-oxo-7-(1H-tetrazol-5-yl)-1H-pyrido[1.2-a]thieno[3,2-d]pyrimidine A mixture of 3,10-dihydro-10-oxo-1H-pyrido[1,2-a]thieno[3.2-d]pyrimidine-7-carbonitrile (0.8 g., 0.003 mol), sodium azide (0.8 g., 0.012 mol) and ammonium chloride (0.07 g., 0.013 mol) in dimethylformamide (100 ml) is heated under nitrogen at 100° C. for 18 hours. The reaction mixture is cooled, poured into ice-water (750 ml), acidified with concentrated hydrochloric acid and stirred for one hour. The precipitate is filtered, washed with water and with acetone. Recrystallization from dimethylformamide gives a crystalline product (0.63 g.), mp 297° C. (dec).

What is claimed is:

1. A compound of the formula

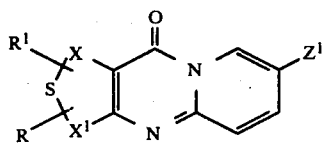

and salts thereof, wherein X is —CH$_2$— and X$^1$ is

—CH$_2$—, X is —CH$_2$CH$_2$— and X$^1$ is a single bond, and X is a single bond and X$^1$ is —CH$_2$CH$_2$—; Z$^1$ is CO$_2$ lower alkyl, cyclic hydrocarbon, cyano, carboxy,

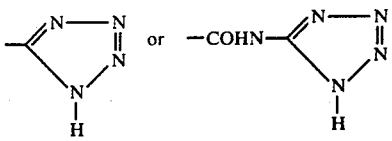

and R and R$^1$ are hydrogen, lower alkyl, cyclic hydrocarbon, chloro, bromo, phenyl or x-substituted phenyl were x is lower alkyl, chloro, fluoro, cyclic hydrocarbon-O-, or lower alkyl —O—.

2. The compound of claim 1 having the name 3,10-dihydro-10-oxo-7-(1H-tetrazol-5-yl)-1H-pyrido[1,2-a]thieno[3,2-d]pyrimidine, and salts thereof.

3. The compound of claim 1 having the name 3,10-dihydro-10-oxo-7-(1H-tetrazol-5-yl)-1H-pyrido[1,2-a]thieno[3,4-d]pyrimidine, and salts thereof.

4. The compound of claim 1 having the name 3,10-dihydro-10-oxo-N-1H-tetrazol-5-yl-1H-pyrido[1,2-a]thieno[3,4-d]pyrimidine-7-carboxamide, and salts thereof.

* * * * *